(12) United States Patent
Penders et al.

(10) Patent No.: US 11,510,607 B2
(45) Date of Patent: Nov. 29, 2022

(54) SYSTEMS AND METHODS FOR MONITORING FETAL WELLBEING

(71) Applicant: Bloom Technologies NV, Genk (BE)

(72) Inventors: Julien Penders, San Francisco, CA (US); Eric Dy, San Francisco, CA (US); Marco Altini, San Francisco, CA (US)

(73) Assignee: BLOOM TECHNOLOGIES NV, Genk (BE)

( * ) Notice: Subject to any disclaimer, the term of this patent is extended or adjusted under 35 U.S.C. 154(b) by 339 days.

(21) Appl. No.: 16/613,621

(22) PCT Filed: May 14, 2018

(86) PCT No.: PCT/IB2018/053355
§ 371 (c)(1),
(2) Date: Nov. 14, 2019

(87) PCT Pub. No.: WO2018/211403
PCT Pub. Date: Nov. 22, 2018

(65) Prior Publication Data
US 2020/0178880 A1    Jun. 11, 2020

Related U.S. Application Data

(60) Provisional application No. 62/506,074, filed on May 15, 2017.

(51) Int. Cl.
*A61B 5/00* (2006.01)
*A61B 5/0205* (2006.01)
(Continued)

(52) U.S. Cl.
CPC ........ *A61B 5/4362* (2013.01); *A61B 5/02055* (2013.01); *A61B 5/6833* (2013.01);
(Continued)

(58) Field of Classification Search
CPC . A61B 5/4362; A61B 5/02055; A61B 5/6833; A61B 5/7267; A61B 5/7275;
(Continued)

(56) References Cited

U.S. PATENT DOCUMENTS 5,042,503 A    8/1991  Torok et al.
5,623,939 A    4/1997  Garfield et al.
(Continued)

FOREIGN PATENT DOCUMENTS

CA    2608497 A1    8/2006
CA    2754721 A1    9/2010
(Continued)

OTHER PUBLICATIONS

Bakris, "A practical approach to achieving recommended blood pressure goals in diabetic patients", Archives of Internal Medicine, vol. 161, Issue 22, 2001, pp. 2661-2667.
(Continued)

*Primary Examiner* — Rex R Holmes
(74) *Attorney, Agent, or Firm* — Aurora Consulting LLC; Kristen J. Hansen; Ashley Sloat

(57) ABSTRACT

A system for monitoring fetal wellbeing over time during pregnancy includes a sensor coupled to a pregnant woman; a processor communicatively coupled to the sensor; and a computer-readable medium having non-transitory, processor-executable instructions stored thereon. Execution of the instructions causes the processor to perform a method including: acquiring a signal from a sensor; processing the signal to identify and extract a parameter of interest from the signal; and analyzing the parameter of interest to determine a degree of fetal wellbeing. The parameter of interest may include one or more of: an average fetal heart rate, an average fetal heart rate variability, a fetal kick or movement count, an average placental oxygenation level, an average placental temperature, an average placental pH, an average amount of amniotic fluid, a fetal heart rate profile, a fetal heart rate variability profile, and a fetal movement profile.

17 Claims, 11 Drawing Sheets

(51) Int. Cl.

| | | |
|---|---|---|
| A61B 5/024 | (2006.01) | |
| A61B 5/053 | (2021.01) | |
| A61B 5/08 | (2006.01) | |
| A61B 5/11 | (2006.01) | |
| A61B 5/145 | (2006.01) | |
| A61B 5/1477 | (2006.01) | |
| A61B 7/04 | (2006.01) | |
| A61B 8/08 | (2006.01) | |
| A61B 5/344 | (2021.01) | |

(52) U.S. Cl.
CPC .......... *A61B 5/7267* (2013.01); *A61B 5/7275* (2013.01); *A61B 5/7282* (2013.01); *A61B 5/0075* (2013.01); *A61B 5/0082* (2013.01); *A61B 5/02405* (2013.01); *A61B 5/02411* (2013.01); *A61B 5/053* (2013.01); *A61B 5/08* (2013.01); *A61B 5/11* (2013.01); *A61B 5/1477* (2013.01); *A61B 5/14539* (2013.01); *A61B 5/14542* (2013.01); *A61B 5/344* (2021.01); *A61B 5/746* (2013.01); *A61B 7/04* (2013.01); *A61B 8/0866* (2013.01); *A61B 2503/02* (2013.01)

(58) Field of Classification Search
CPC ... A61B 5/7282; A61B 5/0075; A61B 5/0082; A61B 5/02405; A61B 5/02411; A61B 5/053; A61B 5/08; A61B 5/11; A61B 5/14539; A61B 5/14542; A61B 5/1477; A61B 5/344; A61B 5/746; A61B 7/04; A61B 8/0866; A61B 2503/02; A61B 5/7264

See application file for complete search history.

(56) References Cited

U.S. PATENT DOCUMENTS

| | | | |
|---|---|---|---|
| 5,776,073 | A | 7/1998 | Garfield et al. |
| 5,954,663 | A | 9/1999 | Gat |
| 6,134,466 | A | 10/2000 | Rosenberg |
| 6,171,263 | B1 | 1/2001 | Sullivan |
| 6,556,977 | B1 | 4/2003 | Lapointe |
| 6,816,744 | B2 | 11/2004 | Garfield et al. |
| 7,285,090 | B2 | 10/2007 | Andre |
| 7,532,923 | B1 | 5/2009 | Hayes-Gill et al. |
| 8,116,855 | B2 | 2/2012 | James et al. |
| 8,229,550 | B2 | 7/2012 | James et al. |
| 8,255,238 | B2 | 8/2012 | Powell et al. |
| 8,398,546 | B2 | 3/2013 | Andre |
| 8,734,296 | B1 | 5/2014 | Brumback |
| D717,674 | S | 11/2014 | Vu et al. |
| 8,880,140 | B2 | 11/2014 | Hayes-Gill et al. |
| D739,284 | S | 9/2015 | Vu et al. |
| D739,775 | S | 9/2015 | Vu et al. |
| D739,776 | S | 9/2015 | Vu et al. |
| D739,777 | S | 9/2015 | Vu et al. |
| D739,778 | S | 9/2015 | Vu et al. |
| D740,706 | S | 10/2015 | Vu et al. |
| D743,819 | S | 11/2015 | Golnik et al. |
| D752,764 | S | 3/2016 | Peters |
| 9,307,923 | B2 | 4/2016 | Peters et al. |
| 9,314,203 | B2 | 4/2016 | Peters |
| 9,392,952 | B1 | 7/2016 | Oz et al. |
| 9,572,504 | B2 | 2/2017 | Oz et al. |
| D781,568 | S | 3/2017 | Workman |
| 9,642,544 | B2 | 5/2017 | Oz et al. |
| 9,713,430 | B2 | 7/2017 | Oz et al. |
| 9,717,412 | B2 | 8/2017 | Roham et al. |
| 9,763,583 | B2 | 9/2017 | Oz et al. |
| 9,999,367 | B2 | 6/2018 | Vullings et al. |
| 10,064,566 | B2 | 9/2018 | Atallah et al. |
| 11,324,437 | B2 | 5/2022 | Mhajna |
| 2001/0039503 | A1 | 11/2001 | Chan |
| 2003/0004403 | A1 | 1/2003 | Drinan et al. |
| 2004/0087840 | A1 | 5/2004 | Main |
| 2005/0267376 | A1 | 12/2005 | Marossero et al. |
| 2007/0191728 | A1 | 8/2007 | Shennib |
| 2007/0255184 | A1 | 11/2007 | Shennib |
| 2007/0260133 | A1 | 11/2007 | Meyer |
| 2008/0029333 | A1 | 2/2008 | Oz |
| 2008/0089184 | A1 | 4/2008 | Palmer |
| 2008/0275309 | A1 | 11/2008 | Andre |
| 2008/0275316 | A1 | 11/2008 | Fink et al. |
| 2009/0036787 | A1 | 2/2009 | James et al. |
| 2009/0143650 | A1 | 6/2009 | Guion-Johnson et al. |
| 2009/0177068 | A1 | 7/2009 | Andre |
| 2009/0192396 | A1 | 7/2009 | Hayes-Gill et al. |
| 2009/0259133 | A1 | 10/2009 | Wolfberg |
| 2009/0299212 | A1 | 12/2009 | Principe et al. |
| 2010/0211594 | A1 | 8/2010 | Penders et al. |
| 2010/0235782 | A1 | 9/2010 | Powell et al. |
| 2010/0274145 | A1 | 10/2010 | Tupin, Jr. et al. |
| 2011/0137913 | A1 | 6/2011 | Bhatti |
| 2011/0172504 | A1 | 7/2011 | Wegerich |
| 2011/0190652 | A1 | 8/2011 | Fink et al. |
| 2011/0237972 | A1 | 9/2011 | Garfield et al. |
| 2011/0251512 | A1 | 10/2011 | Fink et al. |
| 2011/0251817 | A1 | 10/2011 | Burns et al. |
| 2011/0270118 | A1 | 11/2011 | Garfield et al. |
| 2011/0306893 | A1 | 12/2011 | Harrold et al. |
| 2012/0075103 | A1 | 3/2012 | Powell et al. |
| 2012/0150010 | A1 | 6/2012 | Hayes-Gill et al. |
| 2012/0232398 | A1* | 9/2012 | Roham ............... A61B 8/0866 600/453 |
| 2012/0245439 | A1 | 9/2012 | Andre |
| 2012/0265090 | A1 | 10/2012 | Fink et al. |
| 2012/0289789 | A1 | 11/2012 | Jain et al. |
| 2013/0006132 | A1 | 1/2013 | Brody et al. |
| 2013/0030831 | A1 | 1/2013 | Powell et al. |
| 2013/0090538 | A1 | 4/2013 | Garfield et al. |
| 2013/0102857 | A1* | 4/2013 | Wolfberg ............. A61B 5/6823 600/301 |
| 2013/0158367 | A1 | 6/2013 | Andre |
| 2013/0245436 | A1 | 9/2013 | Tupin |
| 2013/0275152 | A1 | 10/2013 | Moore et al. |
| 2013/0316313 | A1 | 11/2013 | Darrow |
| 2014/0045156 | A1 | 2/2014 | Alessandri |
| 2014/0135631 | A1 | 5/2014 | Brumback |
| 2014/0142403 | A1 | 5/2014 | Park |
| 2014/0156228 | A1 | 6/2014 | Park |
| 2014/0163927 | A1 | 6/2014 | Molettiere |
| 2014/0164611 | A1 | 6/2014 | Park |
| 2014/0180169 | A1 | 6/2014 | Peters et al. |
| 2014/0221791 | A1 | 8/2014 | Andre |
| 2014/0235166 | A1 | 8/2014 | Park |
| 2014/0249436 | A1 | 9/2014 | Serguei et al. |
| 2014/0276244 | A1 | 9/2014 | Kamyar |
| 2014/0357961 | A1 | 12/2014 | Natarajan |
| 2014/0379273 | A1 | 12/2014 | Mason |
| 2015/0004912 | A1 | 1/2015 | Diamond et al. |
| 2015/0022366 | A1 | 1/2015 | Vu et al. |
| 2015/0105646 | A1 | 4/2015 | Peters |
| 2015/0374328 | A1 | 12/2015 | Ginestet et al. |
| 2016/0015315 | A1 | 1/2016 | Auphan et al. |
| 2016/0058363 | A1 | 3/2016 | Hayes-Gill et al. |
| 2016/0066827 | A1 | 3/2016 | Workman et al. |
| 2016/0103590 | A1 | 4/2016 | Vu et al. |
| 2016/0139787 | A1 | 5/2016 | Heo |
| 2016/0157717 | A1 | 6/2016 | Gaster et al. |
| 2016/0256132 | A1 | 9/2016 | VandeLaar et al. |
| 2016/0262649 | A1 | 9/2016 | Hayes-Gill et al. |
| 2016/0262687 | A1 | 9/2016 | Vaidyanathan |
| 2016/0331299 | A1 | 11/2016 | Cline |
| 2016/0374608 | A1 | 12/2016 | Dugan |
| 2017/0086709 | A1* | 3/2017 | Khine .................. G16H 40/67 |
| 2017/0156594 | A1 | 6/2017 | Andre |
| 2017/0224268 | A1 | 8/2017 | Dy |
| 2017/0319087 | A1 | 11/2017 | Van De Laar |
| 2018/0296156 | A1 | 10/2018 | Dy |
| 2019/0200916 | A1 | 7/2019 | Hyde et al. |
| 2020/0085365 | A1 | 3/2020 | McDonald et al. |
| 2020/0146614 | A1 | 5/2020 | Cline et al. |

(56) References Cited

U.S. PATENT DOCUMENTS

| | | | |
|---|---|---|---|
| 2020/0155027 A1 | 5/2020 | Lau et al. | |
| 2020/0214618 A1 | 7/2020 | Vullings | |
| 2022/0167911 A1 | 6/2022 | Graham | |

FOREIGN PATENT DOCUMENTS

| | | | |
|---|---|---|---|
| CA | 2765124 A1 | 12/2010 | |
| CA | 2870560 A1 | 10/2013 | |
| EP | 1220640 B1 | 5/2008 | |
| EP | 1941830 A2 | 7/2008 | |
| EP | 1941832 A1 | 7/2008 | |
| EP | 1680018 B1 | 11/2008 | |
| EP | 2451345 A2 | 1/2011 | |
| EP | 1952760 B1 | 4/2012 | |
| EP | 2745774 A1 | 6/2014 | |
| EP | 3011464 A1 | 12/2014 | |
| EP | 2862511 A1 | 4/2015 | |
| EP | 2328471 B1 | 9/2015 | |
| EP | 2997892 A1 | 3/2016 | |
| EP | 2185068 B1 | 9/2016 | |
| WO | 2005110236 A1 | 11/2005 | |
| WO | 2009013245 A1 | 1/2009 | |
| WO | 2009150440 A1 | 12/2009 | |
| WO | 2010105063 A1 | 9/2010 | |
| WO | 2010144413 A1 | 12/2010 | |
| WO | 2011004147 A2 | 1/2011 | |
| WO | 2011094609 A2 | 8/2011 | |
| WO | 2011119757 A2 | 9/2011 | |
| WO | 2011130291 A2 | 10/2011 | |
| WO | 2011130295 A2 | 10/2011 | |
| WO | 2012061827 A1 | 5/2012 | |
| WO | 2012131171 A1 | 10/2012 | |
| WO | 2012142241 A2 | 10/2012 | |
| WO | 2013052612 A2 | 4/2013 | |
| WO | 2013158625 A1 | 10/2013 | |
| WO | 2014035836 A1 | 3/2014 | |
| WO | 2014162135 A1 | 10/2014 | |
| WO | 2014205201 A1 | 12/2014 | |
| WO | 2015013163 A1 | 1/2015 | |
| WO | 2015020886 A1 | 2/2015 | |
| WO | 2015056027 A1 | 4/2015 | |
| WO | 2015063520 A1 | 5/2015 | |
| WO | 2016131630 A1 | 8/2016 | |

OTHER PUBLICATIONS

Faurholt-Jepsen, et al., "Electronic monitoring of psychomotor activity as a supplementary objective measure of depression severity", Nordic Journal of Psychiatry, vol. 69.

Haakstad et al., "Stages of change model for participations in physical activity during pregnancy", Journal of Pregnancy, vol. 2013, 2013, 7 pgs.

Hjortskov, et al., "The effect of mental stress on heart rate variability and blood pressure during computer work", European Journal of Applied Physiology, vol. 92, issue 1-4, pp. 84-89.

Intille, S., "Ubiquitous Computing Technology for Just-in-Time Motivation of Behavior Change", Studies in Health Technology and Informatics, vol. 107, 2004, pp. 1434-1437.

Kenny, et al., "Novel biomarkers for pre-edampsia detected using metabolomics and machine learning", Metabolomics, vol. 1, Issue 3, 2005, pp. 227-234.

Lathia et al., "Smart phones for large-scale behavior change interventions", Proceedings of IEEE Pervasive Computing, 2013, pp. 2-9.

Macmahon, et al., "Blood pressure, stroke, and coronary heart disease: part 1, prolonged differences in blood pressure: prospective observational studies corrected for the regession dilution basis.", Lancet, vol. 335, 1990, pp. 765-774.

Moriya, et al., "Weekly averaged blood pressure is more important than a single-point blood pressure measurement in the risk stratification of dialysis patients", Clinical Jou Nephrol 3, 2008, pp. 416-422.

Pickering, et al., "Ambulatory Blood-Pressure Monitoring", New England Journal of Medicine, vol. 354, 2006, pp. 2368-2374.

Rodriquez-Roisin, "Toward a Consensus Definition for COPD Exacerbations", Chest, vol. 117, issue 5, Suppl 2, 2000, pp. 398S-401S.

Woolf, S.H., "The power of prevention and what it requires", Journal of the American Medical Association, vol. 299, 2008, pp. 2437-2439.

Zhou et al., "Getting Clinicians Involved: Testing Smartphone Applications to Promote Behavior Change in Health Care", May 31, 2012, 5 pages.

Dovetail Care, "Pregnansi", SimilarWeb Ltd, 2016, 7 pages.

Shulgin et al., "Electrohysterographic Signals Processing for Uterine Activity Detection ad Characterization", IEEE XXXIV International Scientific Conference Electronics and Nanotechnology, 2014, pp. 269-272.

Horoba, et al., "Statistical Approach to Analysis of Electrohysterographic Signal", Proceedings of the First Joint BMES/EMBS Conference, Atlanta, GA, 1999, pp. 887.

International Search Report dated Dec. 24, 2014 from International Application PCT/US2014/049280, 4 pgs.

Written Opinion of International Search Report dated Dec. 24, 2014 from International Application PCT/US2014/049280, 15 pgs.

De Lau Hinke et al., "Towards improving uterine electrical activity modeling and electrohysterography: ultrasonic quantification of uterine movements during labor.", Nordic Federation of Societies of Obstetrics and Gynecology, Acta Obstetricia et Gynecologica Scandinavica, 2013, 1323-1326, 92 (11).

Zimmer et al., "The relationship between uterine contractions, fetal movements and fetal heart rate patterns in the active phase of labor", Elsevier Science Publishers B.V. (Biomedical Division), 1987, 89-95, 25 (2).

International Search Report dated May 6, 2016 from International Application PCT/IB2015/002194, 7 pgs.

Written Opinion of International Search Report dated May 6, 2016 from International Application PCT/IB2015/002194, 11 pgs.

European Search Report and Written Opinon of European Search Report for Belgium National Application BE201505056, 18 pgs.

Supplementary European Search Report dated Feb. 17, 2017 for EP 14834450.0, 7 pgs.

Written Opinion of International Search Report dated Dec. 19, 2018 from International Application PCT/IB2018/055394, 12 pgs.

International Search Report dated Dec. 19, 2018 from International Application PCT/IB2018/055394, 8 pgs.

Lange, L. et al. "Velocity and Directionality of the Electrohysterographic Signal Propagation," Plos One, vol. 9, No. 1, Jan. 21, 2014, pp. 1-6.

Maner, W. et al. "Identification of Human Term and Preterm Labor using Artificial Neural Networks on Uterine Electromyography Data," Annuals of Biomedical Engineering, Kluwer Academic Publishers—Plem Publishers, NE, vol. 35, No. 3, Jan. 17, 2007, pp. 465-473.

Penders, J. et al. "Wearable Sensors for Healthier Pregnancies," IEEE, Proceedings of the IEEE, 2015, http://www.ieee.org/publications_standards/publications/rights/index.html "Altini et al. Combining wearable accelerometer and physioloolcal data and energy expenditure estimation. Wireless Health, vol. 13, Nov. 1-3, 2013, 8 pages."

"Altini et al. Personalized energy expenditure estimation using physiological signals normalization during activities of daily living. Physiological Measurement, vol. 35, Aug. 13, 2014, pp. 1797-1811."

"Chiuve et al, Healthy Lifestyle Factors in the Primary Prevention of Coronary Heart Disease Among Men: Benefits Among Users and Nonusers of Lipid-Lowering and Antihypertensive Medications, Circulation Journal of the American Heart Association, vol. 114,160-167, Jul. 2006, 9 pages."

"Luoto et al., Pregnancy and Lifestyle: Short- and Long Teml Effects on Mother's and Her Children's Health, Journal of Pregnancy, Hindawi Publishing Corporation, vol. 2003, May 2013, 2 pages".

* cited by examiner

SYSTEMS AND METHODS FOR MONITORING FETAL WELLBEING

CROSS-REFERENCE TO RELATED APPLICATIONS

This application is the U.S. National Stage Application under 35 U.S.C. 371 for International PCT Patent Application PCT/IB2018/053355, filed May 14, 2018, which claims priority benefits to U.S. Provisional Application Ser. No. 62/506,074, titled "System and Methods for Monitoring Fetal Wellbeing", filed on May 15, 2017, both of which are herein incorporated by reference in their entireties.

BACKGROUND

1. Field

This invention relates generally to the field of fetal health, and more specifically to new and useful systems and methods for monitoring fetal wellbeing.

2. Description of the Related Art

During pregnancy, an expectant mother's ability to accurately monitor the wellbeing of her baby is critical to detecting and potentially treating adverse conditions early. To date, there is no device or system that allows an expectant mother to track the health or wellbeing of her baby over time during pregnancy while going about her day-to-day routine or while staying in the comfort of her own home. Such devices and/or systems are only available to clinical experts in the hospital. Further, current systems and devices are configured to provide information to a physician, nurse, doctor, or other healthcare provider that can read and/or analyze the information and provide recommendations to the expectant mother. However, such information on its face is usually unintelligible to a lay person (e.g., not having clinical or medical training).

Currently, hospitals track fetal health or wellbeing during discrete points in time using fetal movement measurements, fetal heart rate (fHR) measurements, or, more comprehensively, using a BioPhysical Profile (BPP). BPP combines fHR monitoring with fetal ultrasound to assess fetal wellbeing. Because of the use of ultrasound, BPP cannot be performed on a continuous basis. During BPP, a baby's heart rate, breathing, movements, muscle tone, and amniotic fluid level are analyzed and scored by a physician. Typically, BPP is advised for expectant mothers beyond the 32 week mark or, in certain scenarios, after 24 weeks. Further, BPP is typically only available to expectant mothers with high-risk pregnancies.

Another measure of fetal wellbeing that is currently used is a kick count. Physicians request that expectant mothers track fetal movement at home. However, only about one-third of all kicks are actually detected resulting in a high error rate. Further, the expectant mother is prevented from doing anything else except track fetal movements for fear of missing a kick or movement.

As mentioned above, monitoring fetal wellbeing is key in modern obstetrics. While fetal movement and fHR are routinely used as a proxy to fetal wellbeing, accurate, noninvasive long-term monitoring of fetal movement and fHR is challenging. To mitigate the risk, accelerometer-based systems have been developed to tackle common issues in ultrasound movement, and ECG-based systems have been developed to tackle common issues in heart rate monitoring. These systems enable monitoring of fetal movement during pregnancy. However, many of these self-administered, body-worn sensors lack optimal setup, as well as signal processing and machine learning techniques used to detect fetal movement and fHR.

Thus, there is a need for a system and method that allows an expectant mother to receive intelligible data about her developing baby and to monitor fetal wellbeing over time. This invention provides such a new and useful system and method.

SUMMARY

The following is a non-exhaustive listing of some aspects of the present techniques. These and other aspects are described in the following disclosure.

Some aspects include a system for monitoring fetal wellbeing over time during pregnancy, the system includes: a sensor coupled to a pregnant woman; a processor communicatively coupled to the sensor; and a computer-readable medium having non-transitory, processor-executable instructions stored thereon, wherein execution of the instructions causes the processor to perform a method including: acquiring a signal from the sensor; processing the signal to identify and extract a parameter of interest from the signal; and analyzing the parameter of interest to determine a degree of fetal wellbeing.

One aspect of the present disclosure is directed to a system for monitoring fetal wellbeing over time during pregnancy. In some embodiments, a system includes: a sensor coupled to a pregnant woman; a processor communicatively coupled to the sensor; and a computer-readable medium having non-transitory, processor-executable instructions stored thereon. In some embodiments, execution of the instructions causes the processor to perform a method including: acquiring a signal from the sensor; processing the signal to identify and extract a parameter of interest from the signal; and analyzing the parameter of interest to determine a degree of fetal wellbeing.

In some embodiments, the method performed by the processor further includes comparing the parameter of interest to a fetal wellbeing index In some embodiments, the method performed by the processor further includes tracking the parameter of interest over time to develop a personalized fetal wellbeing trend.

In some embodiments, the method performed by the processor further includes: identifying a deviation from the personalized fetal wellbeing trend; and analyzing the deviation to determine whether the deviation is indicative of a change in fetal wellbeing and/or fetal distress.

In some embodiments, the method performed by the processor further includes: tracking the parameter of interest over time; identifying a deviation from a population-level fetal wellbeing trend; and analyzing the deviation to determine whether the deviation is indicative of a change in fetal wellbeing and/or fetal distress. In some embodiments, analyzing the deviation is performed by one of thresholding, a machine learning algorithm, and regression modeling.

In some embodiments, the machine learning algorithm includes one or more of a generalized linear model, support vector machines, and random forests.

In some embodiments, the population-level fetal wellbeing trend is derived from community data in a database. In some embodiments, the community data includes recorded trends, rules, correlations, and observations generated from tracking, aggregating, and analyzing one or more physiological, biological, or activity parameters from a plurality of users.

In some embodiments, the system includes a plurality of sensors.

In some embodiments, acquiring a signal includes acquiring a plurality of signals.

In some embodiments, a plurality of parameters is extracted. In some embodiments, the plurality of parameters comprises physiological, activity, and behavioral parameters.

In some embodiments, the sensor includes one or more sensors configured to measure one or more of fetal movement, fetal heart electrical activity, fetal heart sound, fHR, fetal heart rate variability (fHRV), fetal oxygenation level, an amount of amniotic fluid, placental oxygenation, placental temperature, placental pH, fetal breathing, fetal position, fetal orientation, and fetal distress. In some embodiments, the sensor senses one or more of a biopotential signal, inertial signal, acoustic signal, ultrasound signal, bio-impedance signal, optical signal, near-infrared spectroscopy signal, electrochemical signal, and temperature signal.

In some embodiments, the parameter of interest includes one or more of an average fHR, an average fHRV, an average fetal heart beat, a fetal kick count, a fetal movement count, a fetal oxygenation level, an average placental oxygenation level, an average placental temperature, an average placental pH, an average amount of amniotic fluid, a fHR profile, a fHRV profile, and a fetal movement profile.

In some embodiments, the system further includes a portable and wearable sensor patch, the sensor patch comprising the sensor, the processor, and the computer-readable medium. In some embodiments, the wearable sensor patch further includes a wireless antenna to communicate with a mobile computing device.

In some embodiments, the sensor is positioned on or in a portable and wearable sensor patch, the sensor patch further includes an electronic circuit and a wireless antenna, and wherein the sensor patch is in wireless communication with a mobile computing device comprising the processor and the computer-readable medium.

In some embodiments, the method performed by the processor further includes one or more of generating an alert, providing feedback to the pregnant woman, recommending an action to the pregnant woman, and automatically connecting the pregnant woman with a healthcare provider.

In some embodiments, the method performed by the processor further includes notifying a health care provider of the degree of fetal wellbeing.

In some embodiments, the method performed by the processor further includes determining a probability that the fetus is distressed. In some embodiments, the method performed by the processor further includes determining a degree of certainty around the determined probability. In some embodiments, the method performed by the processor further includes determining a probability that the fetus is healthy.

In some embodiments, analyzing the parameter of interest further includes: comparing the parameter of interest to a threshold.

In some embodiments, if the parameter of interest is above the threshold, there is a higher probability that the fetus is healthy. In some embodiments, if the parameter of interest is below the threshold, there is a higher probability that the fetus is distressed.

In some embodiments, analyzing the parameter of interest further includes: analyzing the parameter of interest using regression models or machine learning algorithms to determine a probability that the fetus is healthy or distressed.

Another aspect of the present disclosure is directed to a computer-implemented method for monitoring fetal wellbeing longitudinally during pregnancy outside of a hospital environment. In some embodiments, the method includes: acquiring a signal from a sensor; processing the signal to identify and extract a parameter of interest from the signal; and analyzing the parameter of interest to determine a degree of fetal wellbeing.

In some embodiments, the method further includes comparing the extracted parameter of interest to a fetal wellbeing index.

In some embodiments, the method further includes tracking the parameter of interest over time to develop a personalized fetal wellbeing trend. In some embodiments, the method further includes: identifying a deviation from the personalized fetal wellbeing trend; and analyzing the deviation to determine whether the deviation is indicative of a change in fetal wellbeing and/or fetal distress.

In some embodiments, the method further includes tracking the parameter of interest over time; identifying a deviation from a population-level fetal wellbeing trend; and analyzing the deviation to determine whether the deviation is indicative of a change in fetal wellbeing and/or fetal distress.

In some embodiments, analyzing the deviation is performed by a machine learning algorithm.

In some embodiments, the machine learning algorithm comprises one or more of a generalized linear model, support vector machines, and random forests.

In some embodiments, the population-level fetal wellbeing trend is derived from community data in a database. In some embodiments, the community data includes recorded trends, rules, correlations, and observations generated from tracking, aggregating, and analyzing one or more physiological, biological, or activity parameters from a plurality of users.

In some embodiments, the method further includes acquiring a plurality of signals.

In some embodiments, the method further includes extracting a plurality of parameters of interest.

In some embodiments, the sensor senses one or more of a biopotential signal, inertial signal, acoustic signal, ultrasound signal, bio-impedance signal, optical signal, near-infrared spectroscopy signal, electrochemical signal, and temperature signal.

In some embodiments, the parameter of interest includes one or more of an average fHR, an average fHRV, an average fetal heart beat, a fetal kick count, a fetal movement count, an average placental oxygenation level, an average placental temperature, an average placental pH, an average amount of amniotic fluid, a fHR profile, a fHRV profile, and a fetal movement profile.

In some embodiments, the method further includes one or more of generating an alert, providing feedback to the pregnant woman, recommending an action to the pregnant woman, and automatically connecting the pregnant woman to a healthcare provider.

In some embodiments, the method further includes notifying a health care provider of the degree of fetal wellbeing.

In some embodiments, the method further includes determining a probability that the fetus is distressed. In some embodiments, the method further includes determining a degree of certainty around the determined probability. In some embodiments, the method further includes determining a probability that the fetus is healthy.

In some embodiments, analyzing the parameter of interest further includes: comparing the parameter of interest to a threshold.

In some embodiments, if the parameter of interest is above the threshold, there is a higher probability that fetus is healthy. In some embodiments, if the parameter of interest is below the threshold, there is a higher probability that the fetus is distressed.

In some embodiments, the method further includes analyzing the parameter of interest using regression models or machine learning algorithms to determine a probability that the fetus is healthy or distressed In some embodiments, the method further includes: tracking a plurality of the parameters of interest over time at a population level; and developing a fetal wellbeing index based on the tracked parameters of interest.

In some embodiments, the method further includes: comparing the extracted parameter of interest to the fetal wellbeing index to determine a degree of fetal wellbeing.

BRIEF DESCRIPTION OF THE DRAWINGS

The above-mentioned aspects and other aspects of the present techniques will be better understood when the present application is read in view of the following figures in which like numbers indicate similar or identical elements.

Figure 1:
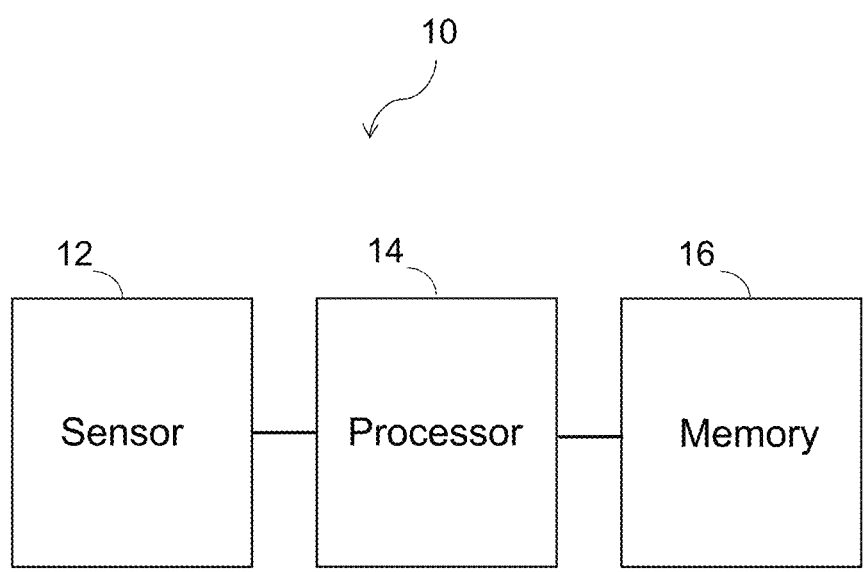
FIG. 1 depicts a block diagram of one embodiment of a system for determining fetal wellbeing in a pregnant female.

While the present techniques are susceptible to various modifications and alternative forms, specific embodiments thereof are shown by way of example in the drawings and will herein be described in detail. The drawings may not be to scale. It should be understood, however, that the drawings and detailed description thereto are not intended to limit the present techniques to the particular form disclosed, but to the contrary, the intention is to cover all modifications, equivalents, and alternatives falling within the spirit and scope of the present techniques as defined by the appended claims.

DETAILED DESCRIPTION OF CERTAIN EMBODIMENTS

To mitigate the problems described herein, the inventors had to both invent solutions and, in some cases just as importantly, reorganize problems overlooked (or not yet foreseen) by others in the fields of fetal health. Indeed, the inventors wish to emphasize the difficulty of recognizing those problems that are nascent and will become more apparent in the future should trends in industry continue as the inventors expect. Further, because multiple problems are addressed, it should be understood that some embodiments are problem-specific, and not all embodiments address every problem with traditional systems described herein or provide every benefit described herein. That said, improvements that solve various permutations of these problems are described below.

Monitoring fetal wellbeing during pregnancy is the most important and complex task of modern obstetrics. As birth outcomes are strongly linked to the development of fetal conditions during pregnancy, several techniques have been proposed to monitor fetal wellbeing (e.g., movement, fHR, etc.). Some methods require hospital stays or trained personnel, e.g., ultrasound, relying on high frequency sound waves being used to generate an image of the fetus that can be used only for a limited amount of time due to safety concerns.

Other approaches to provide monitoring of fetal movement, or an equivalent thereof, such as continuous cardiotocography require cumbersome infrastructure and hospital visits, also involving trained personnel to set up the device and process the produced information. Therefore, the ability of these methods to monitor fetal movement outside of sporadic spot checks in a hospital environment is one of the major causes of concern for passive methods for home-monitoring, such as accelerometer-based solutions.

Many accelerometer-based solutions use one single accelerometer placed on the abdominal area. This involves difference criteria such as the number of sensors used, presence of a reference accelerometer placed outside of the abdominal area, and data analysis. This technique has low sensitivity and specificity. As a result, detection rates are around 50%, which is deemed insufficient by researchers.

Higher detection rates can be accomplished by the addition of a reference accelerometer that monitors maternal movement attributes using an accelerometer placed outside of the abdominal area, therefore, separating fetal movement from maternal movement and providing more accurate detection. The location of the accelerometer is critical since placement on the upper thoracic area may still detect fetal movement and provide unusable results, therefore the accelerometer should be outside of the abdominal and thoracic area. To date, there is no reported studies on the difference in movement detection performance when including or excluding the reference accelerometer. Often, the technique is used as post-processing signaling to discard data more than to inform the classification process. None of which is to suggest that this approach or any other subject matter is disclaimed, as the present techniques may be used to augment various approaches like this.

Data analysis techniques used to date mainly focused on feature extraction by means of time (e.g., the magnitude of the acceleration vector) and frequency domain signal processing techniques. Recently, machine learning techniques, such as using Support Vector Machines, have been used to classify a set of features into a binary problem. While determining optimal features may be a necessary first step, thresholding on a single feature provided poor results. The combining of multiple features and machine learning methods has the potential for more accurate fetal movement detection. Challenges may arise when using supervised learning methods to classify movements. Fetal movements occur only for a short percentage of the time during a measurement period, therefore proper methods such as downsampling of the majority class (i.e., no movement) need to be employed. This evaluation may need to be performed on the entire data stream, not only on subsets of data pre-selected by the user. Another design choice concern is the window size on which to compute features, the choice of classifier, feature selection method, performance metrics used to analyze the system, and the reference system used to validate fetal movement detection algorithms.

As noted above, most studies relied on ultrasound as a reference for fetal movement. While ultrasound is the clinical standard, limitations apply. In some cases, with fetal growth it becomes extremely difficult to fully display the fetus given the limited field of vision of the ultrasound probe, staring at approximately week 20 of the pregnancy. This particular concern may not be a problem during hospital checkups, however moving and re-positioning the probe while measuring small accelerations as reflected on the pregnant women's abdomen is impractical and can easily introduce noise.

Some embodiments mitigate some or all of the problems discussed above, as well as other problems discussed below and those that will be self-evident to one of ordinary skill in the art with knowledge of open issues in the field. Some embodiments may incorporate analyzing of algorithm performance and tradeoffs with respect to a reference for accurate sensor numbering, sensor positioning, and data analysis for effectively detecting fetal movement.

Some embodiments mitigate some or all of the problems discussed above by generating an algorithm that highlights differences in models, for example in the Positive Predictive Value (PPV) by the reduction of false positives in datasets when a reference accelerometer is present, as well as when both short and long time windows are used for feature computation.

Some embodiments mitigate some or all of the problems discussed above by analyzing detected fetal kicks versus actual fetal kicks and highlight how the models perform at different levels, for example, individual fetal kicks at the recording level and overall fetal kicks across the data set. This may allow the ability to accurately identify individual movements over incremental intervals, for example approximately 20 minute intervals.

Some embodiments mitigate some or all of the problems discussed above by clustering movements in three classes, for example low movement, medium movement, and high movement and analyzing the results in terms of the ability of the models to accurately identify gross levels of motion over individual movements.

Another aspect of monitoring fetal wellbeing is fHR and fHRV detection. Most currently used methods of fHR and fHRV detection are not suitable for long-term monitoring. For example, Doppler ultrasound and fetal scalp electrodes are among the most commonly used methods. Doppler ultrasound, while non-invasive, emits energy into the body, which requires consistent supervision, making it unsuitable for continued monitoring of fHR and fHRV. Additionally, Doppler ultrasound measurements still require input from trained medical staff to make informed clinical decisions. Further, for example, fetal scalp electrodes are highly invasive and require rupturing of membranes, so it is only useful during delivery. Because the needle-like electrodes are screwed into the scalp of the fetus to obtain fetal electrocardiogram (fECG) signals, there is a risk of infection and tissue damage. Collectively, widespread use of Doppler ultrasound and fetal scalp electrodes is not desirable for continuous or near continuous monitoring of fetal wellbeing.

Electrophysiological measurements on the maternal abdomen also contain the fECG and enable extraction of fHR. However, the signal has a reduced signal-to-noise ratio (SNR) compared to the use of a fetal scalp electrode, with the maternal ECG (mECG) as the predominant interference. Methods seeking to solve the SNR problems of electrophysiological measurements have drastically improved fHR detection in the non-ambulatory setting, but continuous monitoring of the fetus in an ambulatory setting using these methods remains unfeasible due to its computational complexity.

Some embodiments mitigate some or all the problems discussed above by using a discrete-time continuous wavelet transform to reduce the overall computational complexity, while increasing the R-peak detection quality of the mECG.

Some embodiments mitigate some or all the problems discussed above by increasing R-peak detection quality by segment selection (e.g., heart rate limits, R-R interval, previous segment), threshold determination (e.g., previous threshold, max in segment, SNR estimate), SNR estimation (e.g., height of R-peak, max outside QRS, $\log_2$ of ratio), and peak detection (e.g., first peak greater than threshold, select highest peak within 0.05 to 5 seconds).

Disclosed herein are systems and methods for monitoring fetal wellbeing. In some embodiments, monitoring fetal wellbeing includes monitoring fetal movement, fHR and/or fHRV. In general, the systems and methods described herein include a sensor module used to monitor fetal wellbeing continuously or over time. Results of the monitoring may be provided to the pregnant woman or expectant mother; a gynecologist; obstetrician; pediatrician; other physician; nurse practitioner; veterinarian; other healthcare provider; doula; midwife; other birthing specialist; spouse; partner; parent; sibling; other family member; friend; a healthcare facility administrator; or any other individual with whom the pregnant woman wishes to share such information.

As used herein, "pregnant woman," "pregnant female," or "expectant mother" may be used interchangeably. It will be appreciated by one skilled in the art that each of the embodiments described herein may be used by a pregnant mammal regardless of species.

As used herein, "baby," "fetus," or "developing infant" may be used interchangeably. It will be appreciated by one skilled in the art that each of the embodiments described herein may be used to monitor the wellbeing of the fetus regardless of species.

As used herein, a "parameter of interest" refers to a pattern, feature, characteristic, component, aspect, element, or attribute extracted from a sensor signal that is related to fetal wellbeing. A parameter of interest may include an average fHR, an average fHRV, an average fetal heart beat, a fetal kick count, a fetal movement count, an average placental oxygenation level, an average placental temperature, an average placental pH, an average amount of amniotic fluid, a fHR profile, a fHRV profile, and a fetal movement profile.

As used herein, a "fetal wellbeing index" refers to a composite measure of fetal wellbeing that summarizes and/or rank-orders one or more specific fetal wellbeing observations and/or measurements. It will be appreciated by one skilled in the art that the fetal wellbeing index described herein may be derived from one or a plurality of observations or measurements. Further, it will also be appreciated that a high score on a fetal wellbeing index may indicate a high probability of a healthy or distressed fetus as well as a low score on a fetal wellbeing index may indicate a high probability of a healthy or distressed fetus.

System

In some embodiments, the above described features may be implemented in a system 10 as shown in FIG. 1. It should be emphasized, though, that not all embodiments include all of the above-described features, afford all the above-described benefits, or partially or fully mitigate all of the above-described problems, which is not to suggest that any other description herein is limiting. Rather, multiple, independently useful techniques are described, with various engineering and cost trade-offs, and some embodiments may implement some of those techniques while others not implementing others.

As shown in FIG. 1, in various embodiments, a system 10 for monitoring fetal wellbeing may include at least one sensor 12 in electrical communication with a processor 14 and a computer-readable medium (i.e., memory) 16. FIG. 1 illustrates a functional block diagram, and it is to be appreciated that the various functional blocks of the depicted system 10 need not be separate structural elements. For example, in some embodiments, the processor 14 and memory 16 may be embodied in a single chip or two or more chips.

The sensor 12 detects events (e.g., fetal kicks, fetal movement, etc.), physiological features (e.g., heart rate, placental oxygenation level, etc.) and/or changes in the environment (e.g., an amount of amniotic fluid) of the fetus and provides a corresponding output or signal. In some embodiments, the system 10 includes one sensor 12: in some embodiments, the system 10 includes a plurality of sensors 12. For example, the sensor 12 may include one or more sensors configured to measure: fetal movement, fetal heart electrical activity, fetal heart sound, fHR, fHRV, an amount of amniotic fluid, placental oxygenation, placental temperature, placental pH, fetal breathing, fetal position, fetal orientation, and/or fetal distress.

The sensor 12 of various embodiments is configured for placement on an outer surface of a woman's body. In some embodiments, the sensor 12 is reusable; in other embodiments, the sensor 12 is disposable. In at least some embodiments, the sensor 12 is configured for placement over the belly or abdominal region of a pregnant woman. In some embodiments, the sensor 12 forms a portion of a sensor module. Various sensor module embodiments are described in more detail below with reference to FIGS. 2-8.

The sensor 12 may include a biopotential sensor, an inertial sensor, an acoustic sensor, an ultrasound sensor, a bio-impedance sensor, an optical sensor, a near-infrared spectroscopy sensor, an electrochemical sensor, and/or a temperature sensor. A biopotential sensor interacts with ionic charge carriers and transduces ionic currents into electric currents read by a processor. A biopotential sensor as described herein may include at least one measurement electrode and at least one reference electrode. In some configurations, one reference electrode and a plurality of measurement electrodes are present in the biopotential sensor. A biopotential sensor may measure an ECG, electroencephalogram (EEG) or electromyogram (EMG) of the fetus or expectant mother.

An inertial sensor as described herein includes one or more accelerometers, gyroscopes, and/or magnetometers to measure a specific force (i.e., g-force or mass-specific force), angular rate, and/or magnetic field surrounding the body. For example, an inertial sensor or a plurality of inertial sensors of the system may be used to measure fetal movement, fetal position, and/or fetal orientation.

An acoustic sensor, for example an ultrasound sensor, as described herein uses acoustic waves propagated through a portion of the abdomen (may include a portion of the uterus and/or fetus) of the pregnant women to measure characteristics of the pregnant women, uterus, placenta, fetus, or any other characteristic of the fetus or structure supporting the growth of the fetus. As the acoustic waves propagate through the abdomen, one or more characteristics of the waves change, for example in velocity, amplitude, etc. These changes are monitored by the sensor and output as a sensor signal.

A bio-impedance sensor as described herein uses electrical current to measure, for example a variety of cardiac parameters of the fetus or expectant mother. The cardiac parameters may include stoke volume, heart rate, cardiac output, heart rate variability, or any other parameter known to one of skill in the relevant art. In some embodiments, one or more bio-impedance sensors are used to measure an amount of amniotic fluid. For example, an excessive accumulation of amniotic fluid (i.e., polyhydramnios) or a deficiency in amniotic fluid (i.e., oligohydramnios) may be detected by one or more bio-impedance sensors. One non-limiting example of a bio-impedance sensor includes an impedance plethysmography sensor.

An optical sensor as described herein illuminates one or more areas of the skin and measures changes in light absorption or reflection. For example, an optical sensor may be used to measure oxygen saturation of the placenta, blood flow to various organs or appendages, blood pressure, or pulse. One non-limiting example of an optical sensor includes a photoplethysmogram.

A near-infrared spectroscopy sensor as described herein uses near-infrared light to illuminate one or more areas of the skin and measure changes in electromagnetic absorption in this specific band. It may be used to non-invasively to assess placental function, for example by measuring placental oxygenation, blood flow, sugar level, or pH.

An electrochemical sensor as described herein uses electrochemical reactions to measure the concentrations of specific ions and may be used to measure the acidity or pH of body fluids such as sweat or interstitial fluid.

A temperature sensor as described herein may be used to measure an average placental temperature. Non-limiting examples of temperature sensors include a thermistor and a thermocouple.

Returning to FIG. 1, the processor 14 of FIG. 1 may be a general purpose microprocessor, a digital signal processor (DSP), a field programmable gate array (FPGA), an application specific integrated circuit (ASIC), or other programmable logic device, or other discrete computer-executable components designed to perform the functions described herein. The processor may also be formed of a combination of computing devices, for example, a DSP and a microprocessor, a plurality of microprocessors, one or more microprocessors in conjunction with a DSP core, or any other suitable configuration.

In some embodiments, the processor 14 is coupled, via one or more buses, to the memory 16 in order to read information from, and optionally write information to, the memory 16. The memory 16 may be any suitable computer-readable medium that stores computer-readable instructions for execution by a processor 14. For example, the computer-readable medium may include one or more of RAM, ROM, flash memory, EEPROM, a hard disk drive, a solid state drive, or any other suitable device. In some embodiments, the computer-readable instructions include software stored in a non-transitory format. The software may be programmed into the memory 16 or downloaded as an application onto the memory 16. The software may include instructions for running an operating system and/or one or more programs or applications. When executed by the processor 14, the programs or applications may cause the processor 14 to perform a method of monitoring fetal wellbeing over time during pregnancy. Some such methods are described in more detail elsewhere herein.

Figure 2:
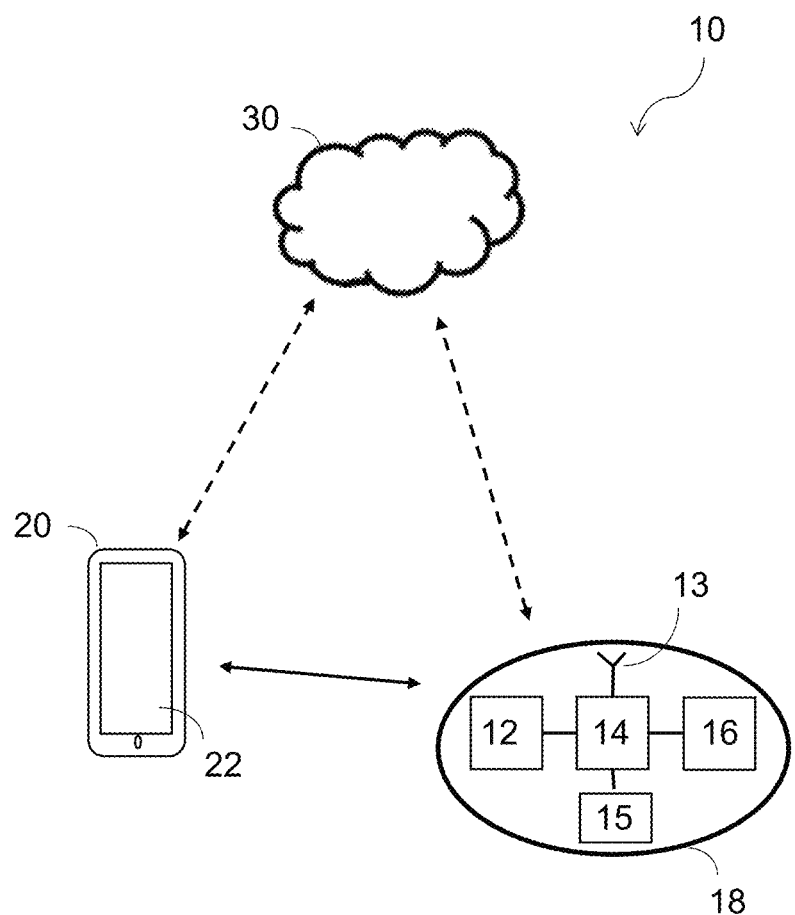
FIG. 2 depicts a block diagram of another embodiment of a system for determining fetal wellbeing in a pregnant female.
Figure 3:
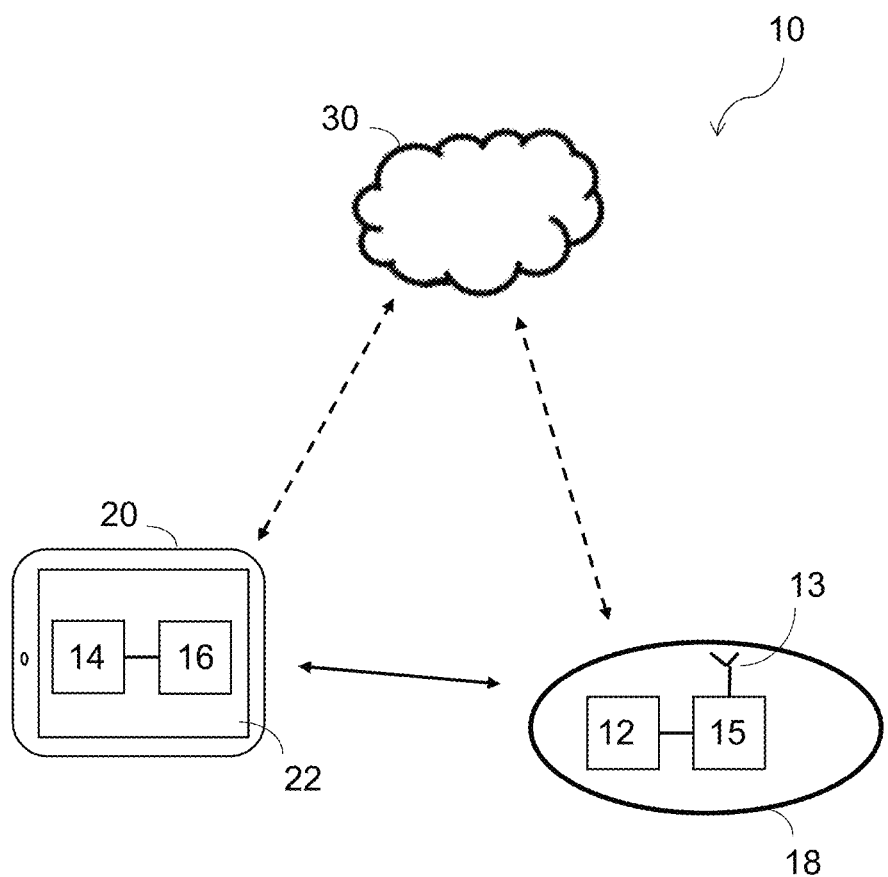
FIG. 3 depicts a block diagram of another embodiment of a system for determining fetal wellbeing in a pregnant female.

As shown in FIG. 2 and FIG. 3, the system 10 may further include a sensor module 18 and a mobile computing device 20. In some embodiments, the system 10 also includes a server 30. In some embodiments, such as the embodiment of FIG. 2, the sensor 12, processor 14, and memory 16 are each positioned on or in the sensor module 18. An electronic circuit 15 and wireless antenna 13 may also be provided on or in the sensor module 18. In such embodiments, signals related to fetal wellbeing are: sensed by the sensor 12; amplified, filtered, digitized and/or otherwise processed by the electronic circuit 15; and analyzed by the processor 14. Execution of instructions stored in memory 16 causes the processor 14 on the sensor module 18 to perform one or more of the methods of monitoring fetal wellbeing described elsewhere herein. Analyzed data may be transmitted via the antenna 13 to one or both of the mobile computing device 20 and the server 30 for visual or audio presentation to a user, additional analysis, and/or storage.

In other embodiments, such as the embodiment of FIG. 3, the sensor 12 is positioned on or in the sensor module 18 with the electronic circuit 15 and wireless antenna 13, while a mobile computing device 20 houses the processor 14 that performs a method of monitoring fetal wellbeing during pregnancy and the memory 16 that stores instructions for performing the method. In such embodiments, signals related to fetal wellbeing are sensed by the sensor 12 and amplified, filtered, digitized and/or otherwise processed by the electronic circuit 15, and the processed signals are transmitted via the antenna 13 to the mobile computing device 20. The processor 14 of the mobile computing device 20 analyzes the processed signals and determines a degree of fetal wellbeing, as described elsewhere herein. The analyzed data may be saved, shared with contacts, or presented to a user via the mobile computing device 20. In some such embodiments, some of or all the analyzed data may be transmitted from the mobile computing device 20 to a server 30 for storage.

In some embodiments, the electronic circuit 15 includes an operational amplifier, a low-pass, high-pass, or band-pass filter, an analog-to-digital (AD) converter, and/or other signal processing circuit components configured to amplify, filter, digitize, and/or otherwise process the physiological signal. The electronic circuit 15 may additionally include a power supply or power storage device, such as a battery or capacitor to provide power to the other electronic components. For example, the electronic circuit 15 may include a rechargeable (e.g., lithium ion) or disposable (e.g., alkaline) battery.

In some embodiments, the antenna 13 includes one or both of a receiver and a transmitter. The receiver receives and demodulates data received over a communication network. The transmitter prepares data according to one or more network standards and transmits data over a communication network. In some embodiments, a transceiver antenna 13 acts as both a receiver and a transmitter for bi-directional wireless communication. As an addition or alternative to the antenna 13, in some embodiments, a databus is provided within the sensor module 18 so that data can be sent from, or received by, the sensor module 18 via a wired connection.

In some embodiments, there is one-way or two-way communication between the sensor module 18 and the mobile computing device 20, the sensor module 18 and the server 30, and/or the mobile computing device 20 and the server 30. The sensor module 18, mobile computing device 20, and/or server 30 may communicate wirelessly using Bluetooth, low energy Bluetooth, near-field communication, infrared, WLAN, Wi-Fi, CDMA, LTE, other cellular protocol, other radiofrequency, or another wireless protocol. Additionally or alternatively, sending or transmitting information between the sensor module 18, the mobile computing device 20, and the server 30 may occur via a wired connection such as IEEE 1394, Thunderbolt, Lightning, FireWire, DVI, HDMI, Serial, Universal Serial Bus, Parallel, Ethernet, Coaxial, VGA, or PS/2.

In some embodiments, the mobile computing device 20 is a computational device wrapped in a chassis that includes a visual display with or without touch responsive capabilities (e.g., Thin Film Transistor liquid crystal display (LCD), in-place switching LCD, resistive touchscreen LCD, capacitive touchscreen LCD, organic light emitting diode (LED), Active-Matrix organic LED (AMOLED), Super AMOLED, Retina display, Haptic/Tactile touchscreen, or Gorilla Glass), an audio output (e.g., speakers), a central processing unit (e.g., processor or microprocessor), internal storage (e.g., flash drive), n number of components (e.g., specialized chips and/or sensors), and n number of radios (e.g., WLAN, LTE, WiFi, Bluetooth, GPS, etc.). In some embodiments, the mobile computing device 20 is a mobile phone, smartphone, smart watch, smart glasses, smart contact lenses, or other wearable computing device, tablet, laptop, netbook, notebook, or any other type of mobile computing device. In some embodiments, the mobile computing device 20 may be a personal computer.

In some embodiments, a display of the mobile computing device 20 may present a user interface for manual data entry by the pregnant female or automatic data entry (e.g., automatic data synchronization) from one or more clinic or hospital records. The user interface may comprise a user profile detailing, for example a conception date, due date, week of pregnancy (e.g., calculated from the conception date and/or due date), starting weight, current weight, weight over time, a sonogram of the fetus, and/or any other information. The profile information may be used, in combination with additional data and/or parameters, to determine a fetal wellbeing threshold or personalized fetal wellbeing trend that will be described in more detail elsewhere herein.

In some embodiments, the server 30 is a database server, application server, internet server, or other remote server. In some embodiments, the server 30 may store user profile data, historical user data, historical community data, algorithms, machine learning models, software updates, or other data. The server 30 may share this data with the mobile computing device 20 or the sensor module 18, and the server 30 may receive newly acquired user data from the sensor module 18 and/or the mobile computing device 20.

A few non-limiting examples of sensor modules 18 are depicted in FIGS. 4-8 and FIG. 12. By comparing the sensor modules of FIGS. 4-8 and FIG. 12, one can easily understand that the sensor module 18 can take many different form factors. The sensor module 18 of various embodiments has many different shapes, sizes, colors, materials, and levels of conformability to the body. The sensor module 18 may connect to, be embedded within, or form a portion of: a patch 40, 42 (e.g., FIGS. 4-6), a strap, belt, or band 44 (e.g., FIG. 7), or a blanket/cover 46 (e.g., FIG. 8), t-shirt, pants, underwear, or other article of clothing or wearable accessory.

Figure 4:
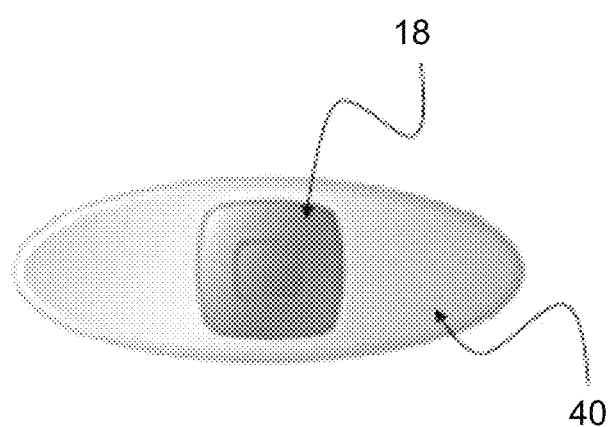
FIG. 4 depicts a top view of one embodiment of a sensor module, which forms a portion of a system for determining fetal wellbeing in a pregnant female.

Turning to FIG. 4, a device for fetal wellbeing monitoring comprises an electrode patch 40 and a sensor module 18, advantageously combined to monitor fetal movement, fHR, fHRV, mHR, and/or at least one channel of uterine contraction signals. The electrode patch 40 and the sensor module 18 may be in one part or may be made of two separate parts. The two separate parts can be provided with a mechanical and electrical system for attaching one to the other, such as a clipping system or a magnet. Other embodiments are described in the description.

Figure 5:
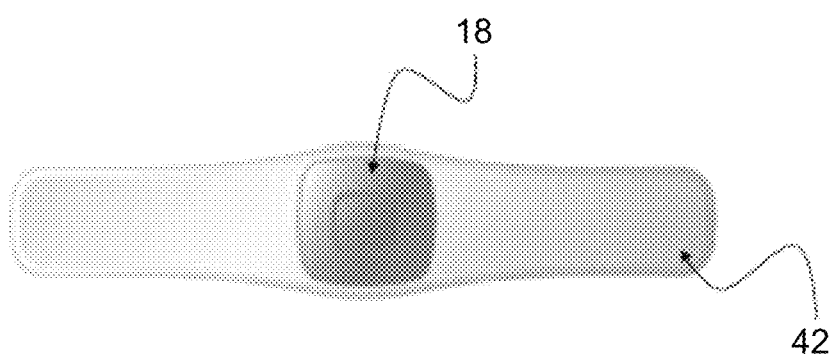
FIG. 5 depicts a top view of another embodiment of a sensor module, which forms a portion of a system for determining fetal wellbeing in a pregnant female.

FIG. 5 illustrates another embodiment of a device for fetal wellbeing monitoring. By comparing FIG. 4 and FIG. 5, one will easily understand that the electrode patch 40, 42 or the sensor module 18 can take many different form factors.

Stated somewhat differently, a device for fetal wellbeing monitoring can take many different shapes, sizes, colors, materials, and levels of conformability to the body. The device may or may not take the form of a plaster. For example, the device may be integrated in a piece of garment, take the form of a piece of clothing or textile, or may take the form of a belt that is worn around the abdomen. For the last three examples, the electrode patch 40, 42 may be an integral part of the piece of garment, clothing or belt, or may be attached to such piece of garment, clothing or belt.

Figure 6:
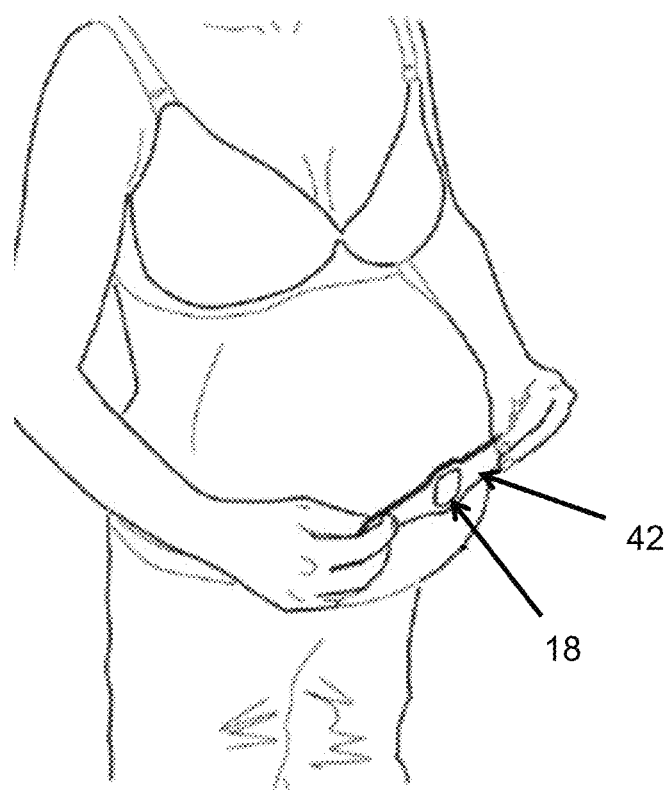
FIG. 6 depicts a perspective view of one embodiment of a sensor module being applied to the abdominal region of a pregnant woman.

FIG. 6 shows another embodiment of a fetal wellbeing monitoring device, wherein the electrode patch 42 and the sensor module 18 can be integrated and encapsulated into one unique part solely making the device. For example, the fetal wellbeing monitoring device of FIG. 6 can have at least three electrodes, including one measurement electrode located on one extremity of the device, one reference electrode located on the other extremity of the device, and one bias electrode in the middle. Such configuration enables the measurement of one channel bio-potential signal, movement signal, fHR signal, and/or fHRV signal along the horizontal direction. In some embodiments, the device of FIG. 6 can have four electrodes, two measurement electrodes located on the two extremities, one reference electrode located in the middle of the device, and one bias electrode located between a measurement electrode and the reference electrode. Advantageously, a variant of the device of FIG. 6 (not shown) can have five electrodes, two measurement electrodes located on the two extremities of the device, one reference electrode located in the middle of the device, one additional measurement electrode located below the reference electrode, at 90 degrees from the line between the first three electrodes, and one bias electrode located between a measurement electrode and the reference electrode. Such configuration enables the measurement of two channels bio-potential signals, movement signals, fHR signals, and/or fHRV signals, one along the horizontal direction and one along the vertical direction. In some embodiments, the electrode patch 42 does not include a reference electrode; rather, the reference electrode is non-existent or positioned on a back on the pregnant female. In a further embodiment, the device can be attached to the body using an adhesive layer. In another embodiment, the adhesive layer can be replaced by the user. In another exemplary embodiment, the device can be attached to the body using a strap or a piece of textile that can maintain the device in contact with the body.

Figure 7:
FIG. 7 depicts a perspective view of another embodiment of a sensor module being applied to the abdominal region of a pregnant woman.

FIG. 7 shows an exemplary embodiment of the fetal wellbeing monitoring device 44, wherein the electrode patch and the sensor module can be integrated in a textile or clothing accessory. Examples of clothing accessories can include, but are not limited to, a shirt, T-shirt, belly-band, a pregnancy support belt or a belt. In some embodiments, a fetal wellbeing monitoring device may have at least three electrodes arranged next to each other so that one measurement electrode is located on the right (respectively left) side of the abdomen, one reference electrode is located on the left (respectively right) side of the abdomen, and one bias electrode in the middle. In some embodiments, the device of FIG. 7 can have a fourth electrode positioned at 90 degrees from the linear arrangement, in the center of the abdomen. This fourth electrode can provide a measurement of the bio-potential signals, movement signals, fHR signals, and/or fHRV signals in the vertical direction. In some embodiments, the device of FIG. 7 can have a fifth electrode positioned at the back of the woman, and providing a signal free of uterine activity and/or maternal movement but carrying physiological and recording artifacts, that can be used in processing the bio-potential signals to obtain cleaner and more accurate EHG, mECG, fECG, fHR, fHRV, and/or fetal movement signals.

Figure 8:
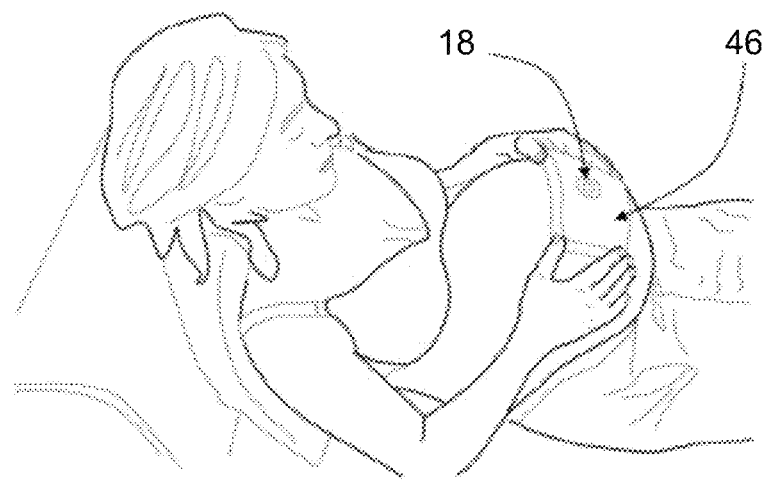
FIG. 8 depicts a perspective view of another embodiment of a sensor module being applied to the abdominal region of a pregnant woman.

FIG. 8 shows another embodiment of a fetal wellbeing monitoring device, wherein the electrode patch 46 and the sensor module 18 can be integrated in an accessory of every-day life that can be integrated in a pillow or in a cover.

Figure 12:
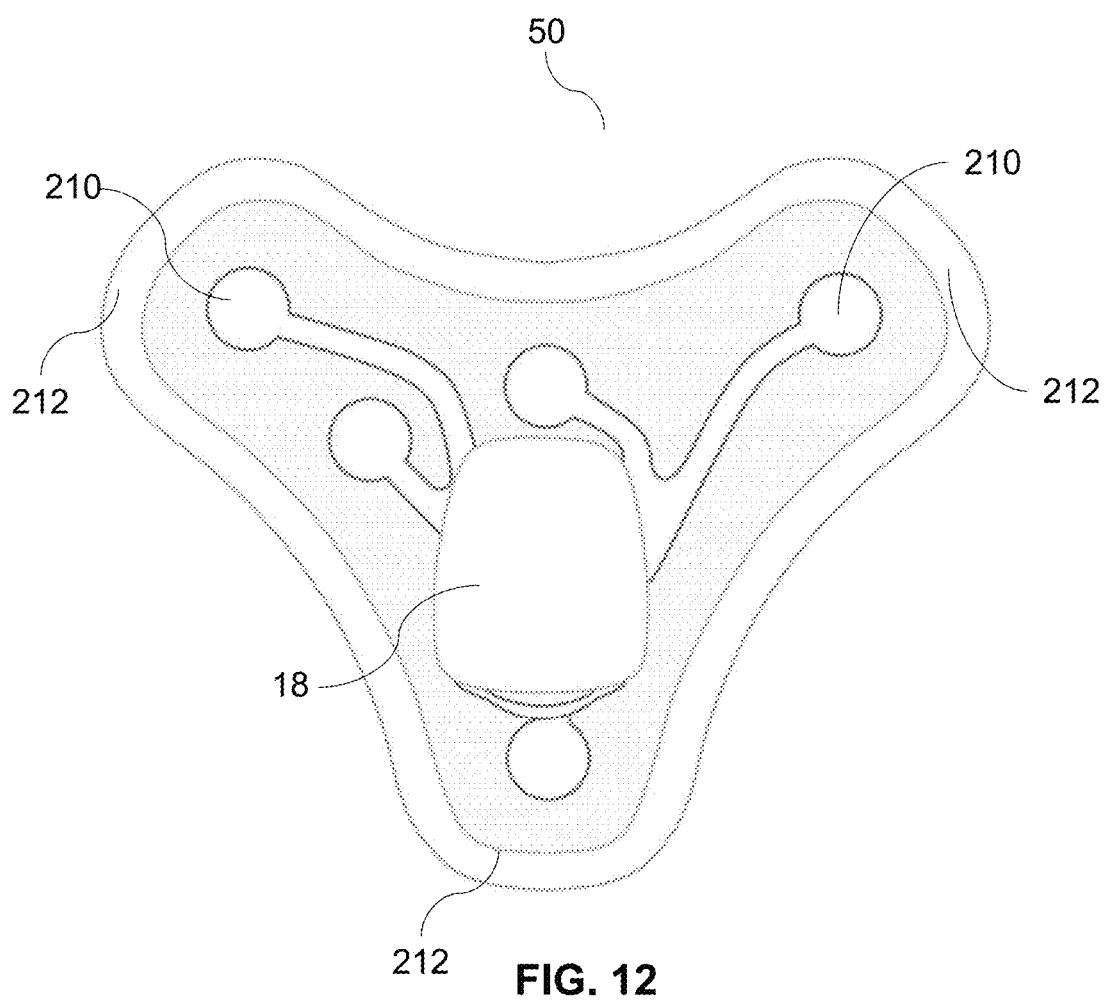
FIG. 12 depicts a perspective view of an embodiment of a fetal wellbeing sensor module, which forms a portion of a system for determining fetal wellbeing in a pregnant female.

In other embodiments, such as the embodiment of FIG. 12, electrode patch 50 includes fetal wellbeing sensor module 18 comprising a plurality of sensors 210 (e.g., accelerometers, gyroscopes, and/or magnetometer), for example, at least 5 sensors. In some embodiments, as shown in FIG. 12, electrode patch 50 has three extremities or lobes 212, each including a sensor 210. Additional sensors 210 are disposed throughout a middle section of the electrode patch 50. As will be apparent from the description elsewhere herein, sensor placement and number are critical for accurately identifying fetal movement, fHR, and/or fHRV. In some cases, the embodiment may include less than five sensors or more than five sensor, e.g., an additional sensor as a reference sensor. In this instance, gross movement may be identified with high efficiency when using a system including a fetal wellbeing sensor module 18 incorporating a plurality of sensors 210.

As it can be seen from FIGS. 4-8 and FIG. 12, a device for fetal wellbeing monitoring is integrated in a small and easy to use form factor that does not require operation by clinical staff. Stated somewhat differently, a device for fetal wellbeing monitoring is advantageously implemented in such a way that a pregnant woman can operate it on her own. The small size and extreme miniaturization can be achieved by a low-power electronics system design, that is a combination of a low-power circuit design, low-power architecture design, and firmware optimization. Low-power system design allows minimizing the size of the battery and therefore can achieve very small size for the overall system. The ease of use can come from a combination of smart electronics and high level of integration. With smart electronics, the device can automatically turn on when it is positioned on the body, or the device can automatically detect contractions, fetal movement, fHR, mHR, and/or fHRV and trigger feedback accordingly, or the system can automatically detect a specific situation—for example the fact that the woman is moving—and adapt its signal processing accordingly. With a high level of integration, the electrode patch can integrate all wires to the electrode, and provide a very simple way for the user to connect the sensor to the electrode patch. Connecting the electrode patch to the sensor module can be done through a magnetic interface, through a snap on mechanism, through a slide on mechanism, through a screw on mechanism, or any other mechanisms that provide a good mechanical and electrical contact between the sensor module and the electrode patch.

The use of an electrode patch improves the reliability of fetal wellbeing monitoring as it is not possible for a user to misplace the different electrodes relative to each other, as they are always in the same relative position. The use of an electrode patch improves the experience and the ease of use of fetal wellbeing monitoring as it does not require attaching multiple electrodes to the abdomen, but only requires attachment of a single electrode patch.

The device can be designed such that it is clear for the pregnant woman how to wear the device, and where to place it. The device can be designed such that it is very easy to put on. For example, the pregnant woman simply has to take the sensor module, attach it to the electrode patch, and wear it.

In some embodiments, the electrode patch comprises at least two electrodes. In an alternative embodiment of the device, the electrode patch can include a third electrode, which can be used for biasing the signal acquisition electronics to the body voltage, or for applying a common mode voltage to the body in order to reduce the measurement noise, a measurement principle also known as right leg drive. In another alternative embodiment of the device, the electrode patch can include additional measurement electrodes. The multiple measurement electrodes can be positioned on different locations on the abdomen, advantageously providing multi-dimensional measurement of the uterine electrical activity, fetal movement, fHR, mHR, and/or fHRV. The electrodes may or may not include conductive gel. Conductive gel may be used to improve the quality of the contact between the body and the electrodes. The electrode patch may or may not be adhesive.

Methods

Some of or all the above-described components or additional or alternate components may function to monitor or determine fetal wellbeing. Some of the methods employed to monitor or detect fetal wellbeing are described below.

Figure 9:
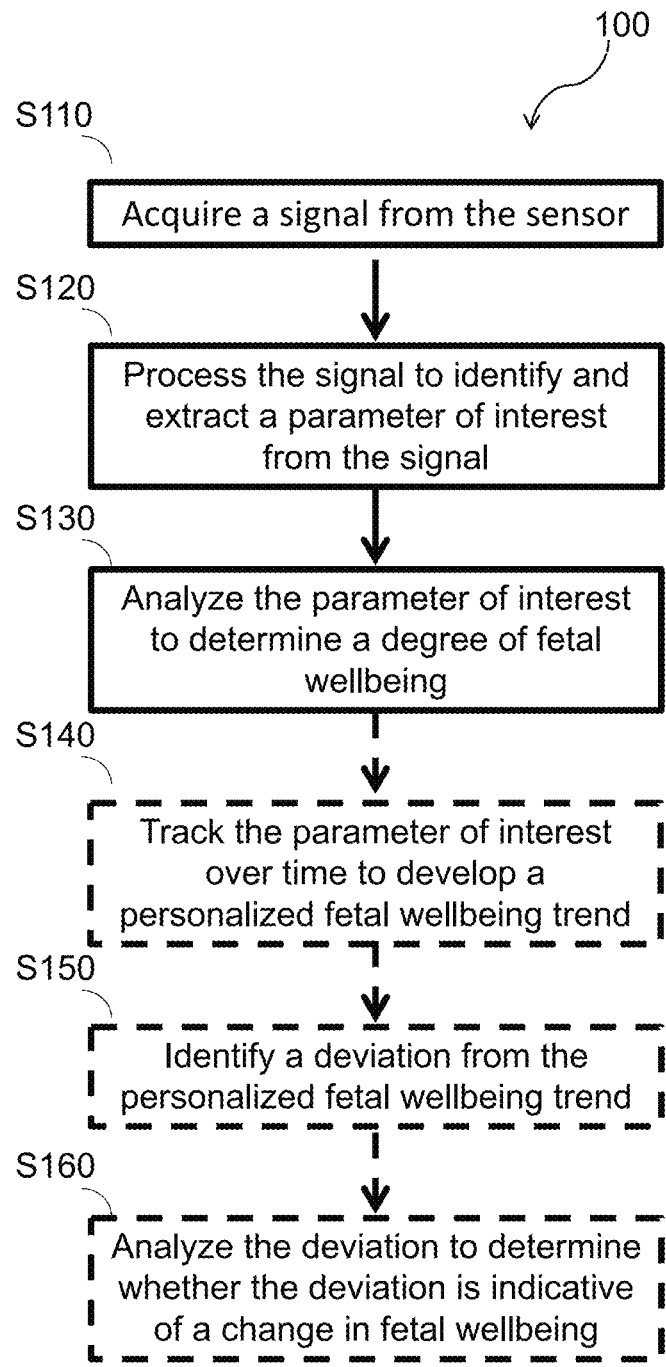
FIG. 9 depicts a flow chart of one embodiment of a computer-implemented method for monitoring fetal wellbeing longitudinally during pregnancy.

As shown in FIG. 9, a computer-implemented method 100 for monitoring fetal wellbeing longitudinally during pregnancy of one embodiment includes acquiring a signal from a sensor S110; processing the signal to identify and extract a parameter of interest from the signal S120; and analyzing the parameter of interest to determine a degree of fetal wellbeing S130. The method functions to monitor and/or determine a degree of fetal wellbeing over time. In some embodiments, the method functions to determine fetal wellbeing by comparing a parameter of interest to a fetal wellbeing index (FIG. 11) or a personalized or population-level fetal wellbeing trend (FIG. 9). The method is used for the fields of maternity and/or fetal health but can additionally or alternatively be used for any suitable applications, clinical or otherwise.

In some embodiments, the degree of fetal wellbeing over time may be over a time interval of a few seconds, for instance an interval of less than 8 seconds, 4 seconds, 2 seconds, 1 second, or 0.5 seconds. In some instances, the fetal movements may be averaged over a longer time interval and captured over shorter time intervals. In some cases, longer time intervals (e.g., 4 seconds) may be set and long enough to average out accelerations due to fetal kicks, but also short enough to limit processing delays and limit maternal movements that may impact algorithm output for longer periods of time intervals. In some instances, variable-length features may reduce false positives. In some embodiments, low-complexity time domain features, for instance, mean, standard deviation, interquartile range, correlation between axis, sum, min, max, and magnitude may be implemented on an embedded device. In some cases, each feature may be computed per axis, per sensor, and/or per window time interval size.

In some embodiments, feature classification may be performed using random forests. In some instances, the low-complexity time domain features may not be selected before classification, in such cases, random forests may pick a subset of the available low-complexity time domain features at each iteration. In some instances, the number of features may be set to select at each iteration to the square root of the total number of features to maintain all information at training phase with respect to other feature selection methods. In such cases where there is a small number of kicks with respect to the total available data (i.e., total kicks from fetal and maternal), class imbalance may be addressed by allowing the random forests classifier to pick a subset of samples during training. The optimal ratio between reference class (i.e., kicks) and majority class (i.e., non-kicks) may be determined by cross-validating and optimizing the F-score, e.g., choosing the ratio that showed optimal F-score. In some instances, all the data may be included from the minority class and one fifth of the majority class data to provide optimal balance.

As shown in FIG. 9, one embodiment of a computer-implemented method 100 for monitoring fetal wellbeing longitudinally during pregnancy includes block S110, which recites acquiring a signal from a sensor. Block S110 functions to measure a feature or characteristic (e.g., fetal heart peak/rate, maternal heart peak/rate, heart rate variability, movement, kick count, etc.) of a fetus or an environment (e.g., an amount of amniotic fluid, a pH of amniotic fluid, placental oxygenation, etc.) surrounding the fetus. For example, acquiring a signal may include: acquiring one or more signals indicative of fetal movement, heart electrical activity, heart sound, heart rate, heart rate variability, an amount of amniotic fluid, placental oxygenation, placental temperature, placental pH, breathing, position, distress, and/or any other feature or characteristic of interest. In various embodiments, the one or more signals are sensed by a sensor having a plurality of electrodes and recorded by a processor into memory.

As shown in FIG. 9, one embodiment of a computer-implemented method 100 for monitoring fetal wellbeing longitudinally during pregnancy includes block S120, which recites processing the signal to identify and extract a parameter of interest from the signal. Block S120 functions to isolate one or more parameters of interest from the signal generated by the sensor. For example, the method may include: amplifying, filtering, digitizing, and/or otherwise processing the sensor signal to isolate a readable signal from a noisy acquired signal. The method may include identifying and/or extracting a parameter of interest or a series of parameters of interest from the sensor signal. The parameter of interest may be, for example, one or more of: average fHR, an average fHRV, an average fetal heart beat, a fetal kick count, a fetal movement count, an average placental oxygenation level, an average placental temperature, an average placental pH, an average amount of amniotic fluid, a fHR profile, a fHRV profile, and a fetal movement profile. In some embodiments, the method includes calculating a mean value, a median value, a percentile, a standard deviation, or other meaningful statistic of the parameter of interest. The parameter of interest may be a physiological parameter (e.g., heart rate, an amount of amniotic fluid, placental oxygenation, etc.) and/or a behavioral parameter (e.g., kick count, fetal movement, fetal movement profile, etc.). In some embodiments, the expectant mother may supplement the data by entering into a user interface of the mobile computing device an observed parameter of interest, for example an observed kick count, fetal position or orientation, other general feeling about the fetus, or information the pregnant woman obtained from a doctor's visit.

In some embodiments, as in block S120, the feature or parameter of interest may be a fHR. The fHR may be detected by a signal from a sensor. In some instances, after preprocessing the detected signal, the maternal heart peaks may be detected and removed from the signal. In this case, the fetal heart peak may be detected from a filtered signal to remove low frequency fluctuation and high frequency artifacts and noise. In some embodiments, the data (i.e., heart rate data) may be convolved with a wavelet function to emphasize the peaks in the frequency band, then the absolute value of the resulting signal may be generated from the data. In some cases, the signal may be analyzed using a short sliding time interval. In some instances, the peak may be determined by passing a threshold of the signal to noise ratio. Once the peak is determined, a new analysis time interval may be defined. In other cases, the current analysis time interval may be increased. The computed peak may be determined with the wavelet power and then optimized in the time domain.

In some embodiments, the determined maternal heart peak may be removed from the signal to determine the fetal heart peak, which may be a magnitude smaller in amplitude. In some instances, to remove the maternal heart peak, a template using the last determined maternal heart peak may be generated. The template may be fitted to the current peak, and the adjusted template from the data may be removed. In some cases, to improve the template, a principal component analysis procedure may be implemented. In this case, a principal component analysis may find the principal components representing the most information among the maternal segments. The first component may be the mean of the signal and the other components may represent the variation of the data from the first component. In this case, the first principal components may be fitted to the data.

In some embodiments, once the maternal heart peak is removed, the heart peak detection algorithm as described above may be completed again with the addition of a wavelet centered at a higher frequency, generating the fetal heart peaks.

As shown in FIG. 9, one embodiment of a computer-implemented method 100 for monitoring fetal wellbeing longitudinally during pregnancy includes block S130, which recites analyzing the parameter of interest to determine a degree of fetal wellbeing. Block S130 functions to singularly assess or aggregate multiple parameters of interest to determine a degree of fetal wellbeing. In some embodiments, thresholding, regression models, and/or machine learning algorithms may be used to determine a probability that the fetus is healthy or distressed, as described in further detail elsewhere herein.

In some embodiments, analyzing the parameter of interest may include detecting fetal kicks by reducing false positives to improve accuracy. In some embodiments, the dataset acquired by a signal from the sensor may be divided between a training set and a validation set. In some cases, the training set may include at least two thirds of the acquired data. In some cases, the acquired data may be randomly sampled, and the validation set may include at least one third of the acquired data. For example, 60 recordings may be used for the training set and 28 recordings may be used for the validation set. In some embodiments, data classification may be organized as a binary classification problem determining fetal kicks from non-fetal kicks (i.e., non-movement, noise, etc.). In some instances, with the binary classification problem and the data imbalance, sensitivity and PPV may be chosen as two metric representations to detect sporadic fetal kicks. In some cases, performance metrics may be determined and computed on the entire data stream for all participants during cross-validation according to true positives (TP), false negatives (FN), and false positives (FP).

In some embodiments, performance measurements may be determined by the following formula:
Sensitivity (Se): Actual Event Recordings Identified by the Model $$Se = \frac{TP}{TP + FN}$$

Positive Predictive Value (PPV): Recordings Identified as an Event, that are Actually the Event:

$$PPV = \frac{TP}{TP + FP}$$

where TP are true positives, FN are false negatives, FP are false positives, and TN are true negatives.

In some embodiments, as shown in FIG. 9, the method 100 optionally includes block S140, which recites tracking the parameter of interest over time to develop a personalized fetal wellbeing trend. A personalized fetal wellbeing trend may include measuring one or more parameters of interest hourly, daily, weekly, monthly, during each trimester of pregnancy or more or less frequently to determine what is "normal" on an individual basis for the fetus. In one non-limiting example, a fetus of an expectant mother may be healthy but the personalized fetal wellbeing trend may show that on average, the fetus has a low kick count, for example due to size of the fetus, uterus volume, an amount of amniotic fluid, etc. Thus, using the personalized fetal wellbeing trend, the expectant mother or a physician may be able to more accurately determine fetal wellbeing on an individual basis.

In some embodiments, during tracking the parameter of interest over time, algorithms may demonstrate improvements in the PPV (i.e., reduction of false positives) when a reference accelerometer is present, as well as when both short and long time intervals are used for feature computation. In some instances, the algorithm may be performed at different levels, for example, computing individual kicks at the recording level and overall across the dataset, to identify the ability of the system to effectively identify individual movements over 20 minute time intervals. In some cases, the system may cluster individual movements into three classes (e.g., low, medium, and high movements) and analyze the results in terms of the system's ability to effectively identify gross level of motion instead of individual movements.

In some embodiments, as shown in FIG. 9, the method 100 optionally includes blocks S150 and S160, which recite identifying a deviation from the personalized fetal wellbeing trend; and analyzing the deviation to determine whether the deviation is indicative of fetal distress and/or a change in fetal wellbeing, respectively. For example, a deviation may be an observed or measured parameter of interest that is above, below, or otherwise aberrant from the personalized fetal wellbeing trend. Using the above non-limiting example, if the fetal kick count drops below the average displayed by the personalized fetal wellbeing trend, the method may include recommending that the pregnant female contact a healthcare provider and/or providing a probability that the fetus is distressed.

Figure 10:
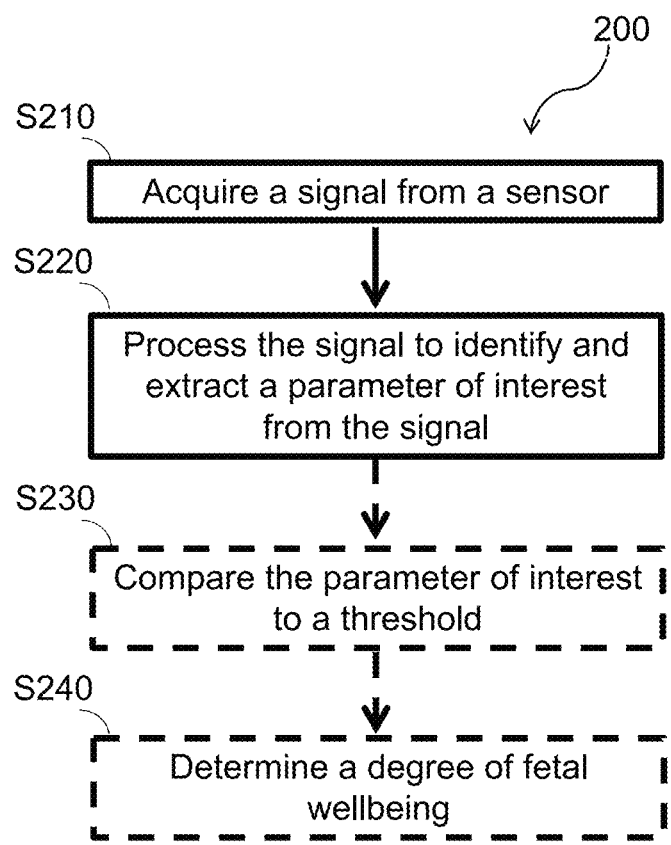
FIG. 10 depicts a flow chart of one embodiment of a computer-implemented method for monitoring fetal wellbeing longitudinally during pregnancy.

As shown in FIG. 10, a computer-implemented method 200 for monitoring fetal wellbeing longitudinally during pregnancy of one embodiment includes acquiring a signal from a sensor S210; processing the signal to identify and extract a parameter of interest from the signal S220; comparing the parameter of interest to a threshold S230; and determining a degree of fetal wellbeing S230. The method functions to determine a degree of fetal wellbeing using thresholding.

As shown in FIG. 10, a computer-implemented method 200 for monitoring fetal wellbeing longitudinally during pregnancy optionally includes blocks S230 and S240, which recite comparing the parameter of interest to a threshold; and determining a degree of fetal wellbeing, respectively. The threshold may be based on historical medical data, community data, personal data, or other empirical data. In some variations, if the parameter of interest is above the threshold, there is a higher probability that the fetus is healthy. Alternatively, if the parameter of interest is below the threshold, there may be a higher probability that the fetus is distressed. For example, for an amount of amniotic fluid, a threshold may be set at the $50^{th}$ percentile, which is dependent on the week of pregnancy (e.g., derived from a profile of the expectant mother in the system). In some embodiments, if the probability indicates that the fetus may be distressed, the method may include notifying a healthcare provider of the expectant mother, recommending a course of action to the expectant mother (e.g., relaxing, contacting a healthcare provider, drinking more water, etc.), providing feedback to the expectant mother (e.g., relax, go for a walk, etc.), and/or automatically connecting the expectant mother with a healthcare provider or an expert. Further, the method may include determining a degree of certainty around the determined probability.

In some embodiments, the method includes using one or more regression models to analyze the parameter of interest and/or to determine a probability that the fetus is healthy or distressed. Regression models are used to predict one variable from one or more other variables. For example, the one or more other variables may be derived from and/or form part of a personalized fetal wellbeing trend, a population-level fetal wellbeing trend, or any other previously or concurrently acquired or measured signals.

In some embodiments, the method includes using machine learning to analyze the parameter of interest and/or to determine a probability that the fetus is healthy or distressed. Machine learning uses algorithms (e.g., generalized linear model, random forests, support vector machines, etc.) to make predictions, for example about fetal wellbeing, based on one or more measured and/or analyzed signals.

Figure 11:
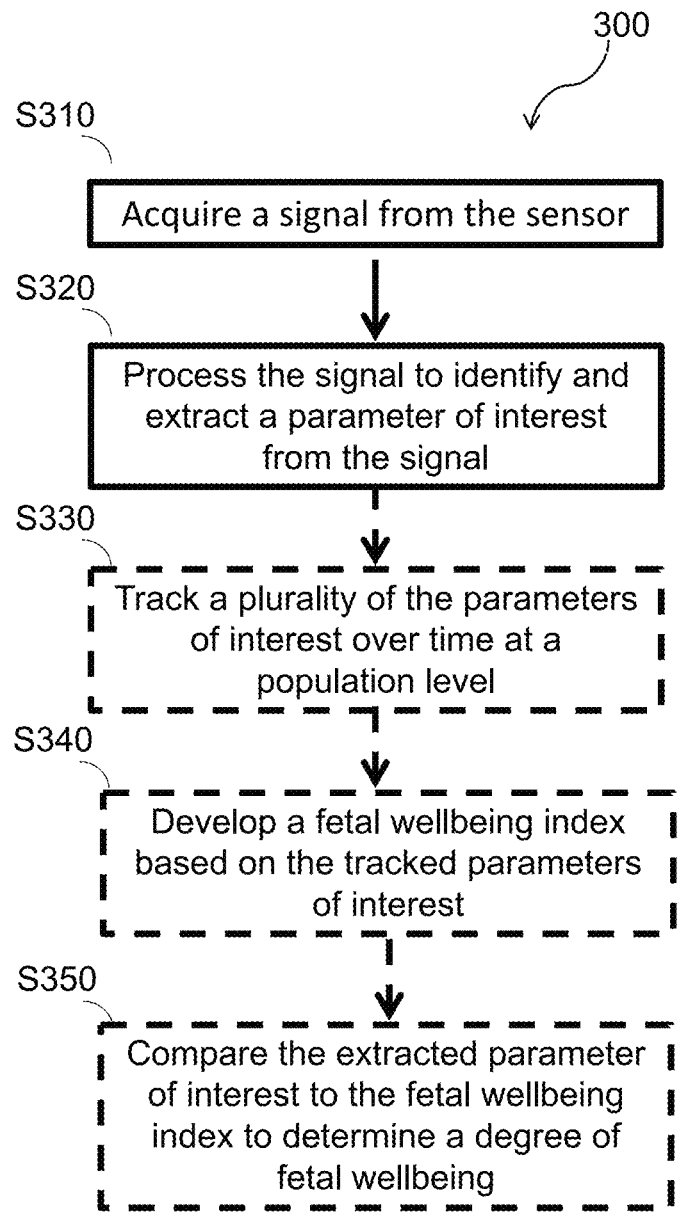
FIG. 11 depicts a flow chart of one embodiment of a computer-implemented method for monitoring fetal wellbeing longitudinally during pregnancy.

As shown in FIG. 11, a computer-implemented method 300 for monitoring fetal wellbeing longitudinally during pregnancy of one embodiment includes acquiring a signal from a sensor S310; processing the signal to identify and extract a parameter of interest from the signal S320; optionally tracking a plurality of the parameters of interest over time at a population level S330; optionally developing a fetal wellbeing index based on the tracked parameters of interest S340; and optionally comparing the extracted parameter of interest to the fetal wellbeing index to determine a degree of fetal wellbeing S350. The method functions to determine a degree of fetal wellbeing by comparing one or more parameters of interest to population-level data, community data, historical data, projected data, empirical data, or any other available data. For example, as shown in block S330, one or more parameters of interest are tracked over time in a population, community, group of mothers, and/or any other setting to develop, create, or otherwise establish a fetal wellbeing index.

As shown in FIG. 11, a computer-implemented method 300 for monitoring fetal wellbeing longitudinally during pregnancy of one embodiment optionally includes block S340, which recites developing a fetal wellbeing index based on the tracked parameters of interest. For example, a fetal wellbeing index may include a scale of one or more parameters, for example from 1-10, where each integer, fraction, or decimal of the scale is linked to a percentile, a historical observation of degrees of fetal wellbeing (e.g., kick count related to fetal wellbeing, fetal movement related to fetal wellbeing, etc.), a measured degree of a fetal feature or characteristic (e.g., heart rate variability related to fetal wellbeing, fetal breathing, etc.), an amount of a measured parameter (e.g., an amount of amniotic fluid related to fetal wellbeing, placental oxygenation related to fetal wellbeing, etc.), or any other parameter.

As shown in FIG. 11, a computer-implemented method 300 for monitoring fetal wellbeing longitudinally during pregnancy of one embodiment optionally includes block S350, which recites comparing the extracted parameter of interest to the fetal wellbeing index to determine a degree of fetal wellbeing. Block S350 functions to assess fetal wellbeing by comparing one or more parameters of interest to a fetal wellbeing index.

In one non-limiting example, a sensor measures a number of fetal kicks in two hours and compares the measured kick count to the fetal wellbeing index. In one embodiment of a fetal wellbeing index, each integer is equal to one kick in a kick count assessment using the systems and methods described herein. Zero to four kicks in two hours may indicate fetal distress, five to nine kicks in two hours may have a higher probability that the fetus is healthy, and ten or more kicks in two hours may indicate a healthy fetus. In some embodiments, the method includes recommending the expectant mother to take specific actions (e.g., drink cold water, lie on back or belly briefly, eat a sweet food, listen to music, press on one side of belly, etc.) to wake-up the baby if the kick count is between five to nine kicks in two hours. In some embodiments, the method includes recommending that the expectant mother contact a healthcare provider if, for example the kick count is below nine kicks in two hours.

In another non-limiting example, each integer is equal to a degree of fHRV measured using the systems and methods described herein. For example, a scale of zero to three may be used in the fetal wellbeing index where: zero equals an undetectable amplitude and absent fHRV; one equals amplitude at five beats per minute (bpm) and minimal fHRV; two equals an amplitude between the range 6 bpm to 25 bpm and moderate fHRV; and three equals an amplitude with a range greater than 25 bpm and marked fHRV.

In some embodiments, a fetal wellbeing index may include, for example, a binary scale or indicator of fetal wellbeing. In one non-limiting example, a fetus positioned in a proper labor orientation receives a one and a fetus not positioned in a proper labor orientation receives a zero (e.g., breach).

In some embodiments, two or more parameters of interest are combined to create the fetal wellbeing index. For example, fetal movement, an amount of amniotic fluid, and an average fHRV (e.g., during each week of pregnancy) may be combined to create a fetal wellbeing index.

In some embodiments, the method includes tracking a plurality of the parameters of interest over time at a population level; and developing a fetal wellbeing index based on the tracked parameters of interest. Data from multiple users of the system may be acquired over time and/or historical datasets may be analyzed to develop a population-level fetal wellbeing trend. The population-level fetal wellbeing trend may be derived from community data in a database, for example recorded trends, rules, correlations, and/or observations generated from tracking, aggregating, and analyzing one or more physiological, biological, or activity parameters from a plurality of users. In some such embodiments, the method includes tracking a parameter of interest over time; identifying a deviation from a population-level fetal wellbeing trend; and analyzing the deviation to determine whether the deviation is indicative of fetal distress and/or a change in fetal wellbeing.

In some variations, analyzing the deviation is performed by a machine learning algorithm. Machine learning algorithms identify patterns, employ computational learning (e.g., learning without being explicitly programmed), and make predictions on data, for example personalized data, community data, and/or population-level data. Non-limiting examples of machine learning algorithms include a generalized linear model, support vector machines, and random forests.

As used in the description and claims, the singular form "a", "an" and "the" include both singular and plural references unless the context clearly dictates otherwise. For example, the term "sensor" may include, and is contemplated to include, a plurality of sensors. At times, the claims and disclosure may include terms such as "a plurality," "one or more," or "at least one;" however, the absence of such terms is not intended to mean, and should not be interpreted to mean, that a plurality is not conceived.

The term "about" or "approximately," when used before a numerical designation or range (e.g., to define a length or pressure), indicates approximations which may vary by (+) or (−) 5%, 1% or 0.1%. All numerical ranges provided herein are inclusive of the stated start and end numbers. The term "substantially" indicates mostly (i.e., greater than 50%) or essentially all of a device, substance, or composition.

In the block diagrams, illustrated components are depicted as discrete functional blocks, but embodiments are not limited to systems in which the functionality described herein is organized as illustrated. The functionality provided by each of the components may be provided by software or hardware modules that are differently organized than is presently depicted, for example such software or hardware may be intermingled, conjoined, replicated, broken up, distributed (e.g. within a data center or geographically), or otherwise differently organized. The functionality described herein may be provided by one or more processors of one or more computers executing code stored on a tangible, non-transitory, machine readable medium. In some cases, notwithstanding use of the singular term "medium," the instructions may be distributed on different storage devices associated with different computing devices, for instance, with each computing device having a different subset of the instructions, an implementation consistent with usage of the singular term "medium" herein. In some cases, third party content delivery networks may host some or all of the information conveyed over networks, in which case, to the extent information (e.g., content) is said to be supplied or otherwise provided, the information may be provided by sending instructions to retrieve that information from a content delivery network.

The reader should appreciate that the present application describes several independently useful techniques. Rather than separating those techniques into multiple isolated patent applications, applicants have grouped these techniques into a single document because their related subject matter lends itself to economics in the application process. But the distinct advantages and aspects of such techniques should not be conflated. In some cases, embodiments address all of the deficiencies noted herein, but it should be understood that the techniques are independently useful, and some embodiments address only a subset of such problems or offer other, unmentioned benefits that will be apparent to those of skill in the art reviewing the present disclosure. Due to cost constraints, some techniques disclosed herein may not be presently claimed and may be claimed in later filings, such as continuation applications or by amending the present claims. Similarly, due to space constraints, neither the Abstract nor the Summary of the Invention sections of the present document should be taken as containing a comprehensive listing of all such techniques or all aspects of such techniques.

It should be understood that the description and the drawings are not intended to limit the present techniques to the particular form disclosed, but to the contrary, the intention is to cover all modifications, equivalents, and alternatives falling within the spirit and scope of the present techniques as defined by the appended claims. Further modifications and alternative embodiments of various aspects of the techniques will be apparent to those skilled in the art in view of this description. Accordingly, this description and the drawings are to be construed as illustrative only and are for the purpose of teaching those skilled in the art the general manner of carrying out the present techniques. It is to be understood that the forms of the present techniques shown and described herein are to be taken as examples of embodiments. Elements and materials may be substituted for those illustrated and described herein, parts and processes may be reversed or omitted, and certain features of the present techniques may be utilized independently, all as would be apparent to one skilled in the art after having the benefit of this description of the present techniques. Changes may be made in the elements described herein without departing from the spirit and scope of the present techniques as described in the following claims. Headings used herein are for organizational purposes only and are not meant to be used to limit the scope of the description.

As used throughout this application, the word "may" is used in a permissive sense (i.e., meaning having the potential to), rather than the mandatory sense (i.e., meaning must). The words "include, "including", and "includes" and the like meaning including, but not limited to. As used throughout this application, the singular forms "a", "an", and "the"

include plural referents unless the content explicitly indicates otherwise. Thus, for example, reference to "an element" or "a element" includes a combination of two or more elements, notwithstanding use of other terms and phrases for one or more elements, such as "one or more". The term "or" is, unless indicated otherwise, non-exclusive, i.e., encompassing both "and" and "or". Terms describing conditional relationships, e.g., "in response to X, Y," "upon X, Y," "if X, Y," "when X, Y," and the like, encompass casual relationships in which the antecedent is a necessary casual condition, the antecedent is a sufficient casual condition, or the antecedent is a contributory casual condition of the consequent, e.g., "state X occurs upon condition Y obtaining" is generic to "X occurs solely upon Y" and "X occurs upon Y and Z." Such conditional relationships are not limited to consequences that instantly follow the antecedent obtaining, as some consequences may be delayed, and in conditional statements, antecedents are connected to their consequents, e.g., the antecedent is relevant to the likelihood of the consequent occurring. Statements in which a plurality of attributes or functions are mapped to a plurality of objects (e.g., one or more processors performing steps A, B, C, and D) encompasses both all such attributes or functions being mapped to all such objects and subsets of the attributes or functions being mapped to subsets of the attributes or functions (e.g., both all processors each performing steps A-D, and a case in which processor 1 performs step A, processor 2 performs step B and part of step C, and processor 3 performs part of step C and step D), unless otherwise indicated. Further, unless otherwise indicated, statements that one value or action is "based on" another condition or value encompass both instances in which the condition or value is the sole factor and instances in which the condition or value is one factor among a plurality of factors. Unless otherwise indicated, statements that "each" instance of some collection have some property should not be rea to exclude cases where some otherwise identical or similar members of a larger collection do not have the property, i.e., each does not necessarily mean each and every. Limitations as to sequence of recited steps should not be read into the claims unless explicitly specified, e.g., with explicit language like "after performing X, performing Y," in contrast to statements that might be improperly argued to imply sequence limitations, like "performing X on items, performing Y on the X'ed items," used for purposes of making claims more readable rather than specifying sequence. Statements referring to "as least Z of A, B, and C," and the like (e.g., "at least Z of A, B, or C"), refer to at least Z of the listed categories (A, B, and C_ and do not require at least Z units in each category. Unless specifically stated otherwise, as apparent from the discussion, it is appreciated that through this specification discussions utilizing terms such as "processing," "computing," "calculating," "determining" or the like refer to actions or processes of a specific apparatus, such as a special purpose computer or a similar special purpose electronic processing/computing device.

As used herein, the term "comprising" or "comprises" is intended to mean that the systems and methods include the recited elements, and may additionally include any other elements. "Consisting essentially of" shall mean that the systems and methods include the recited elements and exclude other elements of essential significance to the combination for the stated purpose. Thus, a system or method consisting essentially of the elements as defined herein would not exclude other materials, features, or steps that do not materially affect the basic and novel characteristic(s) of the claimed invention. "Consisting of" shall mean that the systems and methods include the recited elements and exclude anything more than a trivial or inconsequential element or step. Embodiments defined by each of these transitional terms are within the scope of this disclosure.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The present technique will be better understood with reference to the following enumerated embodiments:

1. A system for monitoring fetal wellbeing over time during pregnancy, the system comprising: a sensor coupled to a pregnant woman; a processor communicatively coupled to the sensor; and a computer-readable medium having non-transitory, processor-executable instructions stored thereon, wherein execution of the instructions causes the processor to perform a method comprising: acquiring a signal from the sensor; processing the signal to identify and extract a parameter of interest from the signal; and analyzing the parameter of interest to determine a degree of fetal wellbeing.

2. The system of embodiment 1, wherein the method performed by the processor further comprises comparing the parameter of interest to a fetal wellbeing index 3. The system of any one of embodiments 1-2, wherein the method performed by the processor further comprises tracking the parameter of interest over time to develop a personalized fetal wellbeing trend.

4. The system of any one of embodiments 1-3, wherein the method performed by the processor further comprise: identifying a deviation from the personalized fetal wellbeing trend; and analyzing the deviation to determine whether the deviation is indicative of a change in fetal wellbeing and/or fetal distress.

5. The system of any one of embodiments 1-4, wherein the method performed by the processor further comprises: tracking the parameter of interest over time; identifying a deviation from a population-level fetal wellbeing trend; and analyzing the deviation to determine whether the deviation is indicative of a change in fetal wellbeing and/or fetal distress.

6. The system of any one of embodiments 1-5, wherein analyzing the deviation is performed by one of thresholding, a machine learning algorithm, and regression modeling.

7. The system of any one of embodiments 1-6, wherein the machine learning algorithm comprises one or more of a generalized linear model, support vector machines, and random forests.

8. The system of any one of embodiments 1-7, wherein the population-level fetal wellbeing trend is derived from community data in a database.

9. The system of any one of embodiments 1-8, wherein the community data comprises recorded trends, rules, correlations, and observations generated from tracking, aggregating, and analyzing one or more physiological, biological, or activity parameters from a plurality of users.

10. The system of any one of embodiments 1-9, wherein the system comprises a plurality of sensors.

11. The system of any one of embodiments 1-10, wherein acquiring a signal comprises acquiring a plurality of signals.

12. The system of Claim 1, wherein a plurality of parameters is extracted.

13. The system of Claim any one of embodiments 1-11, wherein the plurality of parameters comprises physiological, activity, and behavioral parameters.

14. The system of any one of embodiments 1-12, wherein the sensor comprises one or more sensors configured to measure one or more of fetal movement, fetal heart electrical activity, fetal heart sound, fHR, fHRV, an amount of amniotic fluid, placental oxygenation, placental temperature, placental pH, fetal breathing, fetal position, fetal orientation, and fetal distress.

15. The system of any one of embodiments 1-14, wherein the sensor senses one or more of a biopotential signal, inertial signal, acoustic signal, bio-impedance signal, optical signal, near-infrared spectroscopy signal, electrochemical signal and temperature signal.

16. The system of any one of embodiments 1-15, wherein the parameter of interest comprises one or more of an average fHR, an average fHR, an average fetal heart beat, a fetal kick count, a fetal movement count, an average placental oxygenation level, an average placental temperature, an average placental pH, an average amount of amniotic fluid, a fHR profile, a fHR profile, and a fetal movement profile.

17. The system of any one of embodiments 1-16, further comprising a portable and wearable sensor patch, the sensor patch comprising the sensor, the processor, and the computer-readable medium.

18. The system of any one of embodiments 1-17, wherein the wearable sensor patch further comprises a wireless antenna to communicate with a mobile computing device.

19. The system of any one of embodiments 1-18, wherein the sensor is positioned on or in a portable and wearable sensor patch, the sensor patch further comprising an electronic circuit and a wireless antenna, and wherein the sensor patch is in wireless communication with a mobile computing device comprising the processor and the computer-readable medium.

20. The system of any one of embodiments 1-19, wherein the method performed by the processor further comprises one or more of generating an alert, providing feedback to the pregnant woman, recommending an action to the pregnant woman, and automatically connecting the pregnant woman with a healthcare provider.

21. The system of any one of embodiments 1-20, wherein the method performed by the processor further comprises notifying a health care provider of the degree of fetal wellbeing.

22. The system of any one of embodiments 1-21, wherein the method performed by the processor further comprises determining a probability that the fetus is distressed.

23. The system of any one of embodiments 1-22, wherein the method performed by the processor further comprises determining a degree of certainty around the determined probability.

24. The system of any one of embodiments 1-23, wherein the method performed by the processor further comprises determining a probability that the fetus is healthy.

25. The system of any one of embodiments 1-24, wherein the method performed by the processor further comprises determining a degree of certainty around the determined probability.

26. The system of any one of embodiments 1-25, wherein the step of analyzing the parameter of interest further comprises: comparing the parameter of interest to a threshold.

27. The system of any one of embodiments 1-26, wherein if the parameter of interest is above the threshold, there is a higher probability that the fetus is healthy.

28. The system of any one of embodiments 1-27 wherein if the parameter of interest is below the threshold, there is a higher probability that the fetus is distressed.

29. The system of embodiment 28, wherein the step of analyzing the parameter of interest further comprises: analyzing the parameter of interest using regression models or machine learning algorithms to determine a probability that the fetus is healthy or distressed.

30. A computer-implemented method for monitoring fetal wellbeing longitudinally during pregnancy outside of a hospital environment, the method comprising: acquiring a signal from a sensor; processing the signal to identify and extract a parameter of interest from the signal; and analyzing the parameter of interest to determine a degree of fetal wellbeing.

31. The method of embodiment 30, further comprising comparing the extracted parameter of interest to a fetal wellbeing index.

32. The method of any one of embodiments 30-31, further comprising tracking the parameter of interest over time to develop a personalized fetal wellbeing trend.

33. The method of any one of embodiments 30-32, further comprising: identifying a deviation from the personalized fetal wellbeing trend; and analyzing the deviation to determine whether the deviation is indicative of a change in fetal wellbeing and/or fetal distress.

34. The method any one of embodiments 30-33, further comprising: tracking the parameter of interest over time; identifying a deviation from a population-level fetal wellbeing trend; and analyzing the deviation to determine whether the deviation is indicative of a change in fetal wellbeing and/or fetal distress.

35. The method of any one of embodiments 30-34, wherein analyzing the deviation is performed by a machine learning algorithm.

36. The method of any one of embodiments 30-35, wherein the machine learning algorithm comprises one or more of a generalized linear model, support vector machines, and random forests.

37. The method of any one of embodiments 30-36, wherein the population-level fetal wellbeing trend is derived from community data in a database.

38. The method of any one of embodiments 30-37, wherein the community data comprises recorded trends, rules, correlations, and observations generated from tracking, aggregating, and analyzing one or more physiological, biological, or activity parameters from a plurality of users.

39. The method of any one of embodiments 30-38, further comprising acquiring a plurality of signals.

40. The method of any one of embodiments 30-39, further comprising extracting a plurality of parameters of interest.

41. The method of any one of embodiments 30-40, wherein the sensor senses one or more of a biopotential signal, inertial signal, acoustic signal, bio-impedance signal, optical signal, near-infrared spectroscopy signal, electrochemical signal and temperature signal.

42. The method of any one of embodiments 30-41, wherein the parameter of interest comprises one or more of an average fHR, an average fHR, an average fetal heart beat, a fetal kick count, a fetal movement count, an average placental oxygenation level, an average placental temperature, an average placental pH, an average amount of amniotic fluid, a fHR profile, a fHR profile, and a fetal movement profile.

43. The method of any one of embodiments 30-42, further comprising one or more of generating an alert, providing feedback to the pregnant woman, recommending an action to the pregnant woman, and automatically connecting the pregnant woman a healthcare provider.

44. The method of any one of embodiments 30-43, further comprising notifying a health care provider of the degree of fetal wellbeing.

45. The method of any one of embodiments 30-44, further comprising determining a probability that the fetus is distressed.

46. The method of any one of embodiments 30-45, further comprising determining a degree of certainty around the determined probability.

47. The method of any one of embodiments 30-46, further comprising determining a probability that the fetus is healthy.

48. The method of any one of embodiments 30-47, further comprising determining a degree of certainty around the determined probability.

49. The method of any one of embodiments 30-48, wherein the step of analyzing the parameter of interest further comprises: comparing the parameter of interest to a threshold.

50. The method of any one of embodiments 30-49, wherein if the parameter of interest is above the threshold, there is a higher probability that fetus is healthy.

51. The method of any one of embodiments 1-50, wherein if the parameter of interest is below the threshold, there is a higher probability that the fetus is distressed.

52. The method of any one of embodiments 30-51, further comprising analyzing the parameter of interest using regression models or machine learning algorithms to determine a probability that the fetus is healthy or distressed.

53. The method of any one of embodiments 30-52, further comprising: tracking a plurality of the parameters of interest over time at a population level; and developing a fetal wellbeing index based on the tracked parameters of interest.

54. The method of embodiment 53, further comprising: comparing the extracted parameter of interest to the fetal wellbeing index to determine a degree of fetal wellbeing.

What is claimed is:

1. A system for monitoring fetal wellbeing over time during pregnancy, the system comprising:
    a sensor coupled to a pregnant woman;
    a processor communicatively coupled to the sensor; and
    a computer-readable medium having non-transitory, processor-executable instructions stored thereon, wherein execution of the instructions causes the processor to perform a method comprising:
        acquiring a signal from the sensor;
        processing the signal to identify and extract a plurality of parameters of interest from the signal, wherein the plurality of parameters of interest include at least one physiological parameter and at least one behavioral parameter;
        tracking the plurality of parameters of interest to generate a personalized fetal wellbeing trend;
        identifying a deviation from the personalized fetal wellbeing trend, the deviation including a measured change in one or more of the plurality of parameters of interest that is aberrant from the personalized fetal wellbeing trend;
        analyzing the deviation to determine whether the deviation is indicative of a change in fetal wellbeing, the analyzing including determining whether the deviation indicates that a value associated with the at least one behavioral parameter drops below an average value for the at least one behavioral parameter represented in the personalized fetal wellbeing trend; and
        determining, based on the analyzed deviation, a probability that a fetus associated with the pregnancy is in distress.

2. The system of claim 1, wherein the identifying comprises comparing the plurality of parameters of interest to a fetal wellbeing index.

3. The system of claim 1, wherein the method performed by the processor further comprises:
    identifying a second deviation, the second deviation being from a population-level fetal wellbeing trend; and
    analyzing the second deviation to determine whether the second deviation is indicative of a change in fetal wellbeing.

4. The system of claim 3, wherein analyzing the second deviation is performed by one of thresholding, a machine learning algorithm, and regression modeling.

5. The system of claim 4, wherein the machine learning algorithm comprises one or more of: a generalized linear model, support vector machines, and random forests.

6. The system of claim 1, wherein the system comprises a plurality of sensors and wherein acquiring a signal comprises acquiring a plurality of signals.

7. The system of claim 1, wherein the sensor comprises one or more sensors configured to measure one or more of: fetal movement, fetal heart electrical activity, fetal heart sound, fetal heart rate, fetal heart rate variability, fetal oxygenation, an amount of amniotic fluid, placental oxygenation, placental temperature, placental pH, fetal breathing, fetal position, fetal orientation, and fetal distress.

8. The system of claim 1, wherein the sensor senses one or more of: a biopotential signal, inertial signal, acoustic signal, ultrasound signal, bio-impedance signal, optical signal, near-infrared spectroscopy signal, electrochemical signal and temperature signal.

9. The system of claim 1, wherein the plurality of parameters of interest comprises two or more of: an average fetal heart rate, an average fetal heart rate variability, an average fetal heart beat, a fetal kick count, a fetal movement count, a fetal oxygenation level, an average placental oxygenation level, an average placental temperature, an average placental pH, an average amount of amniotic fluid, a fetal heart rate profile, a fetal heart rate variability profile, and a fetal movement profile.

10. The system of claim 1, wherein the generated probability indicates whether the fetus is distressed or healthy and wherein the method performed by the processor further comprises determining a degree of certainty around the probability.

11. The system of claim 1, wherein analyzing the plurality of parameters of interest further comprises:
    comparing the plurality of parameters of interest to a threshold, wherein when one or more of the plurality of parameters of interest are above the threshold, there is a higher probability that the fetus is healthy; and wherein when one or more of the plurality of parameters of interest are below the threshold, there is a higher probability that the fetus is distressed.

12. The system of claim 1, further comprising:
analyzing the plurality of parameters of interest using regression models or machine learning algorithms to determine a probability that the fetus is healthy or distressed.

13. The system of claim 6, wherein the signal comprises a fetal heart rate signal and a plurality of fetal movement signals such that the method performed by the processor comprises:
acquiring the fetal heart rate signal using one or more sensors of the plurality of sensors; and
acquiring a plurality of fetal movement signals from one or more sensors of the plurality of sensors.

14. The system of claim 13, wherein the method performed by the processor further comprises:
classifying an absolute value of the fetal heart rate signal into one of four classes: absent fetal heart rate variability (fHRV), minimal fHRV, moderate fHRV, and marked fHRV;
classifying each of the plurality of fetal movement signals into one of three classes: low movement, medium movement, and high movement;
combining the classified fetal heart rate signal and the classified fetal movement signals; and
comparing the combined signals to a fetal wellbeing index to determine a degree of fetal wellbeing.

15. The system of claim 1, wherein the plurality of parameters of interest comprises at least a fetal movement parameter, an amount of amniotic fluid parameter, and an average fetal heart rate variability (fHRV) parameter.

16. The system of claim 1, further comprising:
generating, based on the probability, a recommendation for a course of action.

17. The system of claim 1, wherein the personalized fetal wellbeing trend is based on a personalized fetal wellbeing index comprising rank ordered observations and measurements derived from historical fetal wellbeing measurements associated with the personalized fetal wellbeing trend.

* * * * *